(12) United States Patent
Francotte et al.

(10) Patent No.: US 7,741,320 B2
(45) Date of Patent: Jun. 22, 2010

(54) CYCLOALKYLATED BENZOTHIADIAZINES, A PROCESS FOR THEIR PREPARATION AND PHARMACEUTICAL COMPOSITIONS CONTAINING THEM

(75) Inventors: Pierre Francotte, Ans (BE); Pascal De Tullio, Liege (BE); Bernard Pirotte, Oupeye (BE); Laurence Danober, Montesson (FR); Pierre Lestage, Le Celle St Cloud (FR); Daniel-Henri Caignard, Boisemont (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 12/459,844

(22) Filed: Jul. 9, 2009

(65) Prior Publication Data

US 2010/0009974 A1 Jan. 14, 2010

(30) Foreign Application Priority Data

Jul. 9, 2008 (FR) ................................... 08 03898

(51) Int. Cl.
C07D 285/22 (2006.01)
A61K 31/5415 (2006.01)
A61P 25/24 (2006.01)
(52) U.S. Cl. ..................... 514/223.2; 544/12
(58) Field of Classification Search .............. 514/223.2; 544/12
See application file for complete search history.

(56) References Cited

FOREIGN PATENT DOCUMENTS

WO 03/031422 4/2003

OTHER PUBLICATIONS

Whitehead, Calvert, et al., "Diuretics. VI. 1,2,4-Benzothiadiazine 1,1-dioxides substituted at 2,3,4- and 7-N-Sulfamoyl positions" Journal of Organic Chemistry, vol. 27, p. 951-956, 1962.
Database caplus [online] Chemical Abstracts Service, "Hypertension. results of treatment [with various drugs]" Database accession No. 1964:12490.
Phillips, Dean, et al., "5'-alkyl-benzothiadiazides: a new subgroup of AMPA receptor modulators with improved affinity" Bioorganic & Medicinal Chemistry, vol. 10, No. 5, p. 1229-1248, 2002.
French Preliminary Search Report for FR0803898 of Feb. 19, 2009.

*Primary Examiner*—Kahsay T Habte
(74) *Attorney, Agent, or Firm*—Hueschen and Sage

(57) ABSTRACT

Compounds of formula (I):

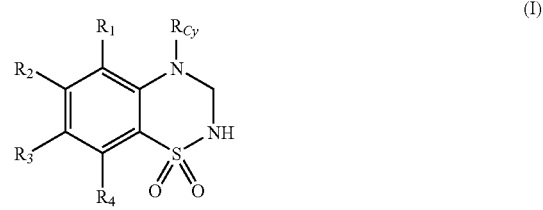

wherein:
$R_{Cy}$, represents an unsubstituted or substituted cycloalkyl group or cycloalkylalkyl group,
$R_1$, $R_2$, $R_3$ and $R_4$, which may be the same or different, each represent a hydrogen or halogen atom or a nitro group; a cyano group; a hydroxy group; an alkoxy group; an alkyl group; an unsubstituted or substituted amino group; a carboxy group; an alkoxycarbonyl group; an aryloxycarbonyl group; an unsubstituted or substituted aminocarbonyl group.

Medicinal products containing the same which are useful in treating or preventing conditions treatable by an AMPA receptor modulator.

15 Claims, No Drawings

CYCLOALKYLATED BENZOTHIADIAZINES, A PROCESS FOR THEIR PREPARATION AND PHARMACEUTICAL COMPOSITIONS CONTAINING THEM

The present invention relates to new cycloalkylated benzothiadiazines, to a process for their preparation, to pharmaceutical compositions containing them and to the use thereof as positive allosteric modulators of AMPA receptors.

It has now been recognised that the excitatory amino acids, very especially glutamate, play a crucial role in the physiological processes of neuronal plasticity and in the mechanisms underlying learning and memory. Pathophysiological studies have clearly shown that a deficit in glutamatergic neurotransmission is closely linked to the development of Alzheimer's disease (Neuroscience and Biobehavioral Reviews, 1992, 16, 13-24; Progress in Neurobiology, 1992, 39, 517-545).

In addition, certain works have in recent years demonstrated the existence of sub-types of excitatory amino acid receptors and their functional interactions (Molecular Neuropharmacology, 1992, 2, 15-31).

Among those receptors, the AMPA (α-amino-3-hydroxy-5-methyl-4-isoxazole-propionic acid) receptor appears to be involved to the greatest extent in the phenomena of physiological neuronal excitability and, especially, in those phenomena involved in memorisation processes. For example, it has been shown that learning is associated with an increase in the binding of AMPA to its receptor in the hippocampus, one of the areas of the brain essential to processes of memory and cognition. Likewise, nootropic agents such as aniracetam have very recently been described as modulating the AMPA receptors of neuronal cells in a positive manner (J. Neurochemistry, 1992, 58, 1199-1204).

In the literature, compounds having a benzamide structure have been described as possessing this same mechanism of action and improving memory performance (Synapse, 1993, 15, 326-329). Compound BA 74, in particular, is the most active of those new pharmacological agents.

Finally, patent specification EP 692 484 describes a benzothiadiazine compound having a facilitating action on the AMPA current, and patent application WO 99/42456 describes, inter alia, certain benzothiadiazine compounds as modulators of AMPA receptors.

The benzothiadiazine compounds to which the present invention relates, besides being new, surprisingly exhibit pharmacological activities with respect to the AMPA receptor that are markedly superior to those of compounds having similar structures described in the prior art.

More specifically, the present invention relates to compounds of formula (I):

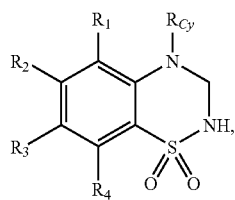

wherein:
$R_{Cy}$ represents:
    a $(C_3$-$C_8)$cycloalkyl group which is unsubstituted or substituted by one or more identical or different groups selected from linear or branched $(C_1$-$C_6)$alkyl which is unsubstituted or substituted by one or more halogen atoms; linear or branched $(C_1$-$C_6)$alkoxy; hydroxy; and amino which is unsubstituted or substituted by one or two linear or branched $(C_1$-$C_6)$alkyl groups;
    or a $(C_3$-$C_8)$cycloalkyl-$(C_1$-$C_6)$alkyl group in which the alkyl moiety is linear or branched and which is unsubstituted or substituted on the cyclic moiety by one or more identical or different groups selected from linear or branched $(C_1$-$C_6)$alkyl which is unsubstituted or substituted by one or more halogen atoms; linear or branched $(C_1$-$C_6)$alkoxy; hydroxy; and amino which is unsubstituted or substituted by one or two linear or branched $(C_1$-$C_6)$alkyl groups;

$R_1$, $R_2$, $R_3$ and $R_4$, which may be the same or different, each represent a hydrogen or halogen atom or a nitro group; a cyano group; a hydroxy group; a thio group; a linear or branched $(C_1$-$C_6)$alkyl group which is unsubstituted or substituted by one or more halogen atoms; a linear or branched $(C_1$-$C_6)$cyanoalkyl group; a linear or branched $(C_1$-$C_6)$hydroxyalkyl group; a linear or branched $(C_1$-$C_6)$alkoxy group which is unsubstituted or substituted by one or more halogen atoms; a linear or branched $(C_1$-$C_6)$alkylthio group; a carboxy group; a linear or branched $(C_1$-$C_6)$alkoxycarbonyl group; an aryloxycarbonyl group; a linear or branched $(C_1$-$C_6)$acyl group; an amino group which is unsubstituted or substituted by one or two linear or branched $(C_1$-$C_6)$alkyl groups or by a linear or branched $(C_1$-$C_6)$acyl group; an aminocarbonyl group which is unsubstituted or substituted by one or two linear or branched $(C_1$-$C_6)$alkyl groups; an arylaminocarbonyl group; or a linear or branched $(C_1$-$C_6)$alkylsulphonylamino group;

to their enantiomers and diastereoisomers when they exist, and also to addition salts thereof with a pharmaceutically acceptable acid or base.

"Aryl" is understood to mean a phenyl group which is unsubstituted or substituted by one or more identical or different groups selected from linear or branched $(C_1$-$C_6)$alkyl which is unsubstituted or substituted by one or more halogen atoms; linear or branched $(C_1$-$C_6)$alkoxy; hydroxy; and amino which is unsubstituted or substituted by one or two linear or branched $(C_1$-$C_6)$alkyl groups.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

Among the pharmaceutically acceptable bases there may be mentioned, without implying any limitation, sodium hydroxide, potassium hydroxide, triethylamine and tert-butylamine.

Preferred $R_{Cy}$ groups are $(C_3$-$C_8)$cycloalkyl groups, more especially a cyclopropyl group. Advantageously, the cyclopropyl group may be substituted by a linear or branched $(C_1$-$C_6)$alkyl group, more especially a methyl group.

Preferred $R_{Cy}$ groups are $(C_3$-$C_8)$cycloalkyl-$(C_1$-$C_6)$alkyl groups in which the alkyl moiety is linear or branched, more especially a cyclopropylmethyl group.

Preferably, the group $R_1$ represents a hydrogen atom or a halogen atom, more especially a fluorine atom.

Preferably, the group $R_2$ represents a hydrogen atom; a halogen atom, more especially a fluorine atom, a chlorine atom or a bromine atom; a cyano group; a carboxy group; or a linear or branched ($C_1$-$C_6$)alkyl group, more preferably a methyl group.

Preferably, the group $R_3$ represents a hydrogen atom; a halogen atom, more especially a fluorine atom, a chlorine atom or a bromine atom; or a linear or branched ($C_1$-$C_6$)alkyl group, more preferably a methyl group.

Preferably, the group $R_4$ represents a hydrogen atom or a halogen atom, more especially a fluorine atom, a chlorine atom or a bromine atom.

More especially preferred are compounds wherein two of the groups $R_1$, $R_2$, $R_3$ and $R_4$ located on the benzene ring each represent a hydrogen atom whilst the two other substituents, which may be the same or different, each represent a group other than a hydrogen atom, preferably selected from halogen atoms, such as a fluorine atom, a chlorine atom or a bromine atom.

Advantageously, more especially preferred are compounds wherein $R_{Cy}$ represents a cyclopropyl group and, two of the groups $R_1$, $R_2$, $R_3$ and $R_4$ located on the benzene ring each represent a hydrogen atom whilst the two other substituents, which may be the same or different, each represent a halogen atom, such as a fluorine atom, a chlorine atom or a bromine atom.

Preferred compounds according to the invention are:
6,7-dichloro-4-cyclopropyl-3,4-dihydro-2H-1,2,4-benzothiadiazine 1,1-dioxide;
8-chloro-4-cyclopropyl-6-fluoro-3,4-dihydro-2H-1,2,4-benzothiadiazine 1,1-dioxide;
8-bromo-4-cyclopropyl-6-fluoro-3,4-dihydro-2H-1,2,4-benzothiadiazine 1,1-dioxide;
6-cyano-4-cyclopropyl-3,4-dihydro-2H-1,2,4-benzothiadiazine 1,1-dioxide;
8-bromo-6-chloro-4-cyclopropyl-3,4-dihydro-2H-1,2,4-benzothiadiazine 1,1-dioxide;
4-cyclopropyl-5-fluoro-3,4-dihydro-2H-1,2,4-benzothiadiazine 1,1-dioxide;
8-bromo-4-cyclopropyl-3,4-dihydro-2H-1,2,4-benzothiadiazine 1,1-dioxide;
4-cyclopropyl-5,7-difluoro-3,4-dihydro-2H-1,2,4-benzothiadiazine 1,1-dioxide;
6-fluoro-4-cyclopropyl-3,4-dihydro-2H-1,2,4-benzothiadiazine 1,1-dioxide;
8-chloro-4-cyclopropyl-7-fluoro-3,4-dihydro-2H-1,2,4-benzothiadiazine 1,1-dioxide;
4-cyclopropyl-3,4-dihydro-6-methyl-2H-1,2,4-benzothiadiazine 1,1-dioxide;
4-cyclopropyl-8-fluoro-3,4-dihydro-2H-1,2,4-benzothiadiazine 1,1-dioxide;
8-chloro-4-cyclopropyl-3,4-dihydro-2H-1,2,4-benzothiadiazine 1,1-dioxide;
6-bromo-4-cyclopropyl-7-fluoro-3,4-dihydro-2H-1,2,4-benzothiadiazine 1,1-dioxide;
6-bromo-4-cyclopropyl-3,4-dihydro-2H-1,2,4-benzothiadiazine 1,1-dioxide;
4-cyclopropyl-6,8-difluoro-3,4-dihydro-2H-1,2,4-benzothiadiazine 1,1-dioxide;
4-cyclopropyl-5,6-difluoro-3,4-dihydro-2H-1,2,4-benzothiadiazine 1,1-dioxide;
4-cyclopropyl-3,4-dihydro-7-methyl-2H-1,2,4-benzothiadiazine 1,1-dioxide;
6-chloro-4-cyclopropyl-3,4-dihydro-2H-1,2,4-benzothiadiazine 1,1-dioxide;
4-cyclopropyl-3,4-dihydro-6-iodo-2H-1,2,4-benzothiadiazine 1,1-dioxide;
6,7-dichloro-4-(1-methyl)cyclopropyl-3,4-dihydro-2H-1,2,4-benzothiadiazine 1,1-dioxide;
4-cyclopropylmethyl-7-fluoro-3,4-dihydro-2H-1,2,4-benzothiadiazine 1,1-dioxide;
6-carboxy-4-cyclopropyl-3,4-dihydro-2H-1,2,4-benzothiadiazine 1,1-dioxide;
4-cyclopropyl-7,8-difluoro-3,4-dihydro-2H-1,2,4-benzothiadiazine 1,1-dioxide;
8-bromo-6-cyano-4-cyclopropyl-3,4-dihydro-2H-1,2,4-benzothiadiazine 1,1-dioxide;
and 7-bromo-4-cyclopropyl-3,4-dihydro-2H-1,2,4-benzothiadiazine 1,1-dioxide.

Addition salts with a pharmaceutically acceptable acid or base of the preferred compounds of the invention form an integral part of the invention.

The invention relates also to a process for the preparation of compounds of formula (I) starting from the compound of formula (II):

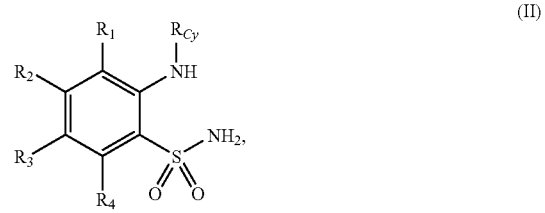

(II)

wherein $R_{Cy}$, $R_1$, $R_2$, $R_3$ and $R_4$ are as defined for formula (I), which is cyclised in the presence of a compound of formula (III):

H—C(OR$_5$)$_3$    (III), wherein $R_5$ represents a linear or branched ($C_1$-$C_6$)alkyl group,
to yield the compound of formula (IV):

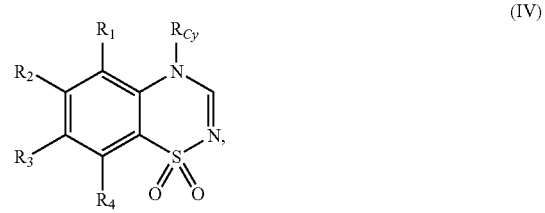

(IV)

wherein $R_{Cy}$, $R_1$, $R_2$, $R_3$ and $R_4$ are as defined hereinbefore,
which is reacted with a reducing agent to yield the compound of formula (I),
a variant in the preparation of compounds of formula (I) consisting of using conventional chemical reactions after carrying out the reduction step on the compound of formula (IV) in order to subsequently change the substituents on the benzene ring,
which compound of formula (I) may then be purified according to a conventional separation technique, is converted, if desired, into its addition salts with a pharmaceutically acceptable acid or base and is separated, where appropriate, into its isomers, if they exist, according to a conventional separation technique.

The present invention relates also to a process for the preparation of compounds of formula (I), which process is characterised in that there is used as starting material a compound of formula (V):

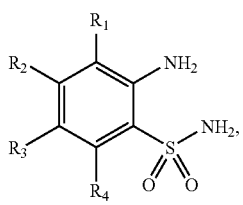

wherein $R_1$, $R_2$, $R_3$ and $R_4$ are as defined hereinbefore,
which is cyclised in the presence of a compound of formula (III) to yield the compound of formula (VI):

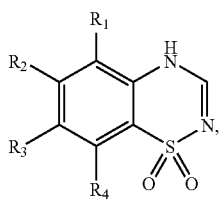

wherein $R_1$, $R_2$, $R_3$ and $R_4$ are as defined hereinbefore,
which is reacted with a compound of formula (VII):

$$Y—R_{Cy} \qquad (VII),$$

wherein $R_{Cy}$ is as defined hereinbefore and Y represents a leaving group selected from iodine and bromine atoms and tosylate, mesylate and triflate groups to yield the compound of formula (IV),
which is reacted with a reducing agent to yield the compound of formula (I),
a variant in the preparation of compounds of formula (I) consisting of using conventional chemical reactions after carrying out the reduction step on the compound of formula (IV) in order to subsequently change the substituents on the benzene ring,
which compound of formula (I) may then be purified according to a conventional separation technique, is converted, if desired, into its addition salts with a pharmaceutically acceptable acid or base and is separated, where appropriate, into its isomers, if they exist, according to a conventional separation technique.

The compounds of formula (II) and of formula (V) are readily accessible to the person skilled in the art using conventional chemical reactions or chemical reactions described in the literature.

The compounds of formula (IV) are new and also form part of the invention as synthesis intermediates for compounds of formula (I).

The compounds of formula (I) according to the invention have AMPA receptor-activating properties which make them of use in the treatment or prevention of disorders of memory and cognition that are associated with age, with syndromes of anxiety or depression, with progressive neurodegenerative diseases, with Alzheimer's disease, with Parkinson's disease, with Pick's disease, with Huntington's chorea, with Korsakoff's disease, with schizophrenia, with the sequelae of acute neurodegenerative diseases, with frontal lobe and subcortical dementias, with the sequelae of ischaemia and with the sequelae of epilepsy.

The invention relates also to pharmaceutical compositions comprising, as active ingredient, at least one compound of formula (I) with one or more appropriate, inert, non-toxic excipients. Among the pharmaceutical compositions according to the invention there may be mentioned more especially those that are suitable for oral, parenteral (intravenous or subcutaneous) or nasal administration, tablets or dragees, sublingual tablets, capsules, lozenges, suppositories, creams, ointments, dermal gels, injectable preparations and drinkable suspensions.

The useful dosage can be varied according to the nature and severity of the disorder, the administration route and also the age and weight of the patient and ranges from 0.01 to 1000 mg per day in one or more administrations.

The Examples that follow illustrate the invention but do not limit it in any way.

The starting materials used are products that are known or that are prepared according to known operating procedures.

The structures of the compounds described in the Examples were determined according to the usual spectrophotometric techniques (infrared, NMR, mass spectrometry).

EXAMPLE 1

6,7-dichloro-4-cyclopropyl-3,4-dihydro-2H-1,2,4-benzothiadiazine 1,1-dioxide

Step A: 4,5-dichloro-2-fluorobenzenesulphonamide

In a 500 mL round-bottom flask, a portion of glacial acetic acid (30 mL) is saturated for 30 minutes with a current of gaseous sulphur dioxide. To the resulting solution there is added a solution of cupric chloride (1.5 g) in water (10 mL) (suspension A). 4,5-Dichloro-2-fluoroaniline (5 g) is dissolved in a mixture of glacial acetic acid (30 mL) and concentrated hydrochloric acid (15 mL). The resulting solution is cooled to −5° C. on a bath of ice and salt. A solution of sodium nitrite (2.5 g) in water (10 mL) is then added dropwise with constant stirring. The resulting mixture is slowly added to suspension A and is stirred on an ice bath for 15 minutes. The mixture is then poured into a mixture of water (200 mL) and ether (200 mL). The ethereal phase is separated off and washed with water (100 mL). The organic phase is concentrated to dryness by distillation under reduced pressure and the residue is re-dissolved in dioxane (25 mL). The solution is poured slowly, whilst stirring, into a mixture of concentrated ammonia (25 mL) and water (10 mL) cooled on an ice bath. After 30 minutes, the solution is evaporated to dryness by distillation under reduced pressure and the residue obtained is dissolved in methanol. The methanolic solution is treated with absorbent carbon and filtered and the filtrate is evaporated to dryness. The residue is recrystallised from a methanol/water mixture.

Melting point: 144-145° C.

Step B:
4,5-dichloro-2-cyclopropylaminobenzenesulphonamide

A solution of 4,5-dichloro-2-fluorobenzenesulphonamide (3 g) in dioxane (30 mL) to which cyclopropylamine (3 mL) has been added is heated at 100-110° C. in a hermetically closed vessel for 24 hours. The solvent and the excess of amine are removed by distillation under reduced pressure and the residue is dissolved in methanol (20 mL). The methanolic solution is cooled on an ice bath, and water (60 mL) is added.

The precipitate obtained (the title product) is collected by filtration, washed with water and dried. It is used in the following Step without being otherwise purified.

Step C: 6,7-dichloro-4-cyclopropyl-4H-1,2,4-benzothiadiazine 1,1-dioxide

In a round-bottom flask, a mixture of 4,5-dichloro-2-cyclopropylaminobenzenesulphonamide from the Step above (2.5 g) and ethyl orthoformate (25 mL) is heated in the open state at 150° C. for 1 hour. The suspension obtained is cooled on an ice bath, and the insoluble material is collected by filtration, washed with ether and dried. The solid is re-dissolved in a mixture of acetone and methanol in the hot state and the hot solution is treated with absorbent carbon and then filtered and concentrated to dryness. The residue is recrystallised from methanol.

Melting point: 260-262° C.

Step D: 6,7-dichloro-4-cyclopropyl-3,4-dihydro-2H-1,2,4-benzothiadiazine 1,1-dioxide Finely ground NaBH$_4$ (1 g) is added to a solution of 6,7-dichloro-4-cyclopropyl-4H-1,2,4-benzothiadiazine 1,1-dioxide from the Step above (1.9 g) in isopropanol (50 mL) and then heated at 50-55° C. for 5-10 minutes. The solvent is removed by evaporation under reduced pressure. The residue is taken up in water (50 mL) and brought to acid pH by adding 6N HCl. The title product is extracted with dichloromethane (3×30 mL). The organic phase is dried over MgSO$_4$ and filtered. The filtrate is evaporated to dryness and the residue obtained is recrystallised from methanol/water 1/1 (60 mL).

Melting point: 174-176° C.

EXAMPLE 2

4-cyclopropyl-3,4-dihydro-7-methyl-2H-1,2,4-benzothiadiazine 1,1-dioxide

Step A: 2-fluoro-5-methylbenzenesulphonamide

The expected product is obtained according to the process described in Step A of Example 1, starting from 2-fluoro-5-methylaniline.

Melting point: 118-120° C.

Step B: 2-cyclopropylamino-5-methylbenzenesulphonamide

The expected product is obtained according to the process described in Step B of Example 1 (heating time: 72 hours).

Step C: 4-cyclopropyl-7-methyl-4H-1,2,4-benzothiadiazine 1,1-dioxide

The expected product is obtained according to the process described in Step C of Example 1 (heating time: 3 hours).

Melting point: 192-195° C.

Step D: 4-cyclopropyl-3,4-dihydro-7-methyl-2H-1,2,4-benzothiadiazine 1,1-dioxide The expected product is obtained according to the process described in Step D of Example 1.

Melting point: 144-145° C.

EXAMPLE 3

6-chloro-4-cyclopropyl-7-fluoro-3,4-dihydro-2H-1,2,4-benzothiadiazine 1,1-dioxide

Step A: 4-chloro-2,5-difluorobenzenesulphonamide

The expected product is obtained according to the process described in Step A of Example 1, starting from 4-chloro-2,5-difluoroaniline.

Melting point: 154-157° C.

Step B: 4-chloro-2-cyclopropylamino-5-fluorobenzenesulphonamide

The expected product is obtained according to the process described in Step B of Example 1.

Step C: 6-chloro-4-cyclopropyl-7-fluoro-4H-1,2,4-benzothiadiazine 1,1-dioxide The expected product is obtained according to the process described in Step C of Example 1 (heating time: 2 hours).

Melting point: 205-206° C.

Step D: 6-chloro-4-cyclopropyl-7-fluoro-3,4-dihydro-2H-1,2,4-benzothiadiazine 1,1-dioxide The expected product is obtained according to the process described in Step D of Example 1.

Melting point: 170-171° C.

EXAMPLE 4

4-cyclopropyl-7-fluoro-3,4-dihydro-2H-1,2,4-benzothiadiazine 1,1-dioxide

Step A: 2,5-difluorobenzenesulphonamide

The expected product is obtained according to the process described in Step A of Example 1, starting from 2,5-difluoroaniline.

Melting point: 135-137° C.

Step B: 2-cyclopropylamino-5-fluorobenzenesulphonamide

The expected product is obtained according to the process described in Step B of Example 1 (heating time: 96 hours).

Step C: 4-cyclopropyl-7-fluoro-4H-1,2,4-benzothiadiazine 1,1-dioxide

The expected product is obtained according to the process described in Step C of Example 1 (heating time: 24 hours, at 130° C.).

Melting point: 170-172° C.

Step D: 4-cyclopropyl-7-fluoro-3,4-dihydro-2H-1,2,
4-benzothiadiazine 1,1-dioxide The expected product is obtained according to the process described in Step D of Example 1.
Melting point: 163-164° C.

EXAMPLE 5

7-chloro-4-cyclopropyl-3,4-dihydro-2H-1,2,4-benzothiadiazine 1,1-dioxide

Step A: 5-chloro-2-fluorobenzenesulphonamide

The expected product is obtained according to the process described in Step A of Example 1, starting from 5-chloro-2-fluoroaniline.
Melting point: 135-136° C.

Step B:
5-chloro-2-cyclopropylaminobenzenesulphonamide

The expected product is obtained according to the process described in Step B of Example 1.

Step C:
7-chloro-4-cyclopropyl-4H-1,2,4-benzothiadiazine
1,1-dioxide

In a sealed autoclave, a mixture of 2-cyclopropylaminobenzenesulphonamide from the Step above (2.5 g) and ethyl orthoformate (25 mL) is heated at 150° C. for 96 hours. The mixture is cooled on an ice bath, and the insoluble material is collected by filtration, washed with ether and dried. The solid is re-dissolved in a mixture of acetone and methanol in the hot state and the hot solution is treated with absorbent carbon and then filtered and concentrated to dryness. The residue is recrystallised from methanol.
Melting point: 229-231° C.

Step D: 7-chloro-4-cyclopropyl-3,4-dihydro-2H-1,2,
4-benzothiadiazine 1,1-dioxide The expected product is obtained according to the process described in Step D of Example 1.
Melting point: 159-161° C.

EXAMPLE 6

4-cyclopropyl-6-fluoro-3,4-dihydro-2H-1,2,4-benzothiadiazine 1,1-dioxide

Step A: 2,4-difluorobenzenesulphonamide

The expected product is obtained according to the process described in Step A of Example 1, starting from 2,4-difluoroaniline.
Melting point: 155-157° C.

Step B:
2-cyclopropylamino-4-fluorobenzenesulphonamide

The expected product is obtained according to the process described in Step B of Example 1.

Step C:
4-cyclopropyl-6-fluoro-4H-1,2,4-benzothiadiazine
1,1-dioxide

The expected product is obtained according to the process described in Step C of Example 1 (heating time: 10 hours, at 130° C.).
Melting point: 199-202° C.

Step D: 4-cyclopropyl-6-fluoro-3,4-dihydro-2H-1,2,
4-benzothiadiazine 1,1-dioxide The expected product is obtained according to the process described in Step D of Example 1.
Melting point: 164-165° C.

EXAMPLE 7

6-chloro-4-cyclopropyl-3,4-dihydro-2H-1,2,4-benzothiadiazine 1,1-dioxide

Step A: 4-chloro-2-fluorobenzenesulphonamide

The expected product is obtained according to the process described in Step A of Example 1, starting from 4-chloro-2-fluoroaniline.
Melting point: 104-106° C.

Step B:
4-chloro-2-cyclopropylaminobenzenesulphonamide

The expected product is obtained according to the process described in Step B of Example 1.

Step C:
6-chloro-4-cyclopropyl-4H-1,2,4-benzothiadiazine
1,1-dioxide

The expected product is obtained according to the process described in Step C of Example 1 (heating time: 5 hours, at 130° C.).
Meting point: 239-242° C.

Step D: 6-chloro-4-cyclopropyl-3,4-dihydro-2H-1,2,
4-benzothiadiazine 1,1-dioxide The expected product is obtained according to the process described in Step D of Example 1.
Meting point: 174-176° C.

EXAMPLE 8

4-cyclopropyl-7-trifluoromethyl-3,4-dihydro-2H-1,2,
4-benzothiadiazine 1,1-dioxide Step A:
2-fluoro-5-trifluoromethylbenzenesulphonamide The expected product is obtained according to the process described in Step A of Example 1, starting from 2-fluoro-5-trifluoromethylaniline.
Melting point: 128-130° C.

Step B: 2-cyclopropylamino-5-trifluoromethylbenzenesulphonamide

The expected product is obtained according to the process described in Step B of Example 1.

Step C: 4-cyclopropyl-7-trifluoromethyl-4H-1,2,4-benzothiadiazine 1,1-dioxide

The expected product is obtained according to the process described in Step C of Example 1 (heating time: 5 hours, at 130° C.).
Melting point: 160-162° C.

Step D: 4-cyclopropyl-7-trifluoromethyl-3,4-dihydro-2H-1,2,4-benzothiadiazine 1,1-dioxide The expected product is obtained according to the process described in Step D of Example 1.
Melting point: 155-157° C.

EXAMPLE 9

4-cyclopropyl-3,4-dihydro-2H-1,2,4-benzothiadiazine 1,1-dioxide

Step A: 2-fluorobenzenesulphonamide

The expected product is obtained according to the process described in Step A of Example 1, starting from 2-fluoroaniline.
Melting point: 160-162° C.

Step B: 2-cyclopropylaminobenzenesulphonamide

The expected product is obtained according to the process described in Step B of Example 1 (heating time: 96 hours).

Step C: 4-cyclopropyl-4H-1,2,4-benzothiadiazine 1,1-dioxide

The expected product is obtained according to the process described in Step C of Example 1 (heating time: 5 hours, at 130° C.).
Melting point: 191-194° C.

Step D: 4-cyclopropyl-3,4-dihydro-2H-1,2,4-benzothiadiazine 1,1-dioxide

The expected product is obtained according to the process described in Step D of Example 1.
Meting point: 165-166° C.

EXAMPLE 10

7-cyano-4-cyclopropyl-3,4-dihydro-2H-1,2,4-benzothiadiazine 1,1-dioxide

Step A: 5-cyano-2-fluorobenzenesulphonamide

The expected product is obtained according to the process described in Step A of Example 1, starting from 5-cyano-2-fluoroaniline.
Melting point: 195-196-C Step B: 5-cyano-2-cyclopropylaminobenzenesulphonamide The expected product is obtained according to the process described in Step B of Example 1.

Step C: 7-cyano-4-cyclopropyl-4H-1,2,4-benzothiadiazine 1,1-dioxide

The expected product is obtained according to the process described in Step C of Example 1 (heating time: 3 hours, at 130° C.).
Melting point: 268-270° C.

Step D: 7-cyano-4-cyclopropyl-3,4-dihydro-2H-1,2,4-benzothiadiazine 1,1-dioxide

The expected product is obtained according to the process described in Step D of Example 1.
Melting point: 259-261° C.

EXAMPLE 11

6-bromo-4-cyclopropyl-7-trifluoromethyl-3,4-dihydro-2H-1,2,4-benzothiadiazine 1,1-dioxide Step A: 4-bromo-2-fluoro-5-trifluoromethylbenzenesulphonamide The expected product is obtained according to the process described in Step A of Example 1, starting from 4-bromo-2-fluoro-5-trifluoromethylaniline.

Step B: 4-bromo-2-cyclopropylamino-5-trifluoromethylbenzenesulphonamide

The expected product is obtained according to the process described in Step B of Example 1.

Step C: 6-bromo-4-cyclopropyl-7-trifluoromethyl-4H-1,2,4-benzothiadiazine 1,1-dioxide The expected product is obtained according to the process described in Step C of Example 1 (heating time: 3 hours, at 130° C.).
Melting point: 204-206° C.

Step D: 6-bromo-4-cyclopropyl-7-trifluoromethyl-3,4-dihydro-2H-1,2,4-benzothiadiazine 1,1-dioxide The expected product is obtained according to the process described in Step D of Example 1.
Melting point: 186-189° C.

EXAMPLE 12

6-bromo-5-chloro-4-cyclopropyl-3,4-dihydro-2H-1,2,4-benzothiadiazine 1,1-dioxide Step A: 4-bromo-3-chloro-2-fluorobenzenesulphonamide The expected product is obtained according to the process described in Step A of Example 1, starting from 4-bromo-3-chloro-2-fluoroaniline.

Step B: 4-bromo-3-chloro-2-cyclopropylaminobenzenesulphonamide

The expected product is obtained according to the process described in Step B of Example 1.

Step C: 6-bromo-5-chloro-4-cyclopropyl-4H-1,2,4-benzothiadiazine 1,1-dioxide

The expected product is obtained according to the process described in Step C of Example 1 (heating time: 3 hours, at 130° C.).
Melting point: 199-201° C.

Step D: 6-bromo-5-chloro-4-cyclopropyl-3,4-dihydro-2H-1,2,4-benzothiadiazine 1,1-dioxide The expected product is obtained according to the process described in Step D of Example 1.
Melting point: 128-131° C.

EXAMPLE 13

4-cyclopropyl-5-trifluoromethyl-3,4-dihydro-2H-1,2,4-benzothiadiazine 1,1-dioxide Step A:
2-fluoro-3-trifluoromethylbenzenesulphonamide The expected product is obtained according to the process described in Step A of Example 1, starting from 2-fluoro-3-trifluoromethylaniline.
Melting point: 112-114° C.

Step B: 2-cyclopropylamino-3-trifluoromethylbenzenesulphonamide

The expected product is obtained according to the process described in Step B of Example 1.

Step C: 4-cyclopropyl-5-trifluoromethyl-4H-1,2,4-benzothiadiazine 1,1-dioxide

The expected product is obtained according to the process described in Step C of Example 1 (heating time: 5 hours, at 130° C.).
Melting point: 180-182° C.

Step D: 4-cyclopropyl-5-trifluoromethyl-3,4-dihydro-2H-1,2,4-benzothiadiazine 1,1-dioxide The expected product is obtained according to the process described in Step D of Example 1.
Melting point: 165-167° C.

EXAMPLE 14

8-chloro-4-cyclopropyl-6-fluoro-3,4-dihydro-2H-1,2,4-benzothiadiazine 1,1-dioxide Step A: 2-chloro-4,6-difluorobenzenesulphonamide The expected product is obtained according to the process described in Step A of Example 1, starting from 2-chloro-4,6-difluoroaniline.
Melting point: 116-120° C.

Step B: 2-chloro-6-cyclopropylamino-4-fluorobenzenesulphonamide

The expected product is obtained according to the process described in Step B of Example 1.

Step C: 8-chloro-4-cyclopropyl-6-fluoro-4H-1,2,4-benzothiadiazine 1,1-dioxide

The expected product is obtained according to the process described in Step C of Example 1 (heating time: 3 hours, at 130° C.).
Melting point: 252-255° C.

Step D: 8-chloro-4-cyclopropyl-6-fluoro-3,4-dihydro-2H-1,2,4-benzothiadiazine 1,1-dioxide The expected product is obtained according to the process described in Step D of Example 1.
Melting point: 190-192° C.

EXAMPLE 15

8-chloro-4-cyclopropyl-3,4-dihydro-7-methyl-2H-1,2,4-benzothiadiazine 1,1-dioxide Step A:
2-chloro-6-fluoro-3-methylbenzenesulphonamide The expected product is obtained according to the process described in Step A of Example 1, starting from 2-chloro-6-fluoro-3-methylaniline.

Step B: 2-chloro-6-cyclopropylamino-3-methylbenzenesulphonamide

The expected product is obtained according to the process described in Step B of Example 1.

Step C: 8-chloro-4-cyclopropyl-7-methyl-4H-1,2,4-benzothiadiazine 1,1-dioxide

The expected product is obtained according to the process described in Step C of Example 1 (heating time: 24 hours, at 130° C.).
Melting point: 218-223° C.

Step D: 8-chloro-4-cyclopropyl-3,4-dihydro-7-methyl-2H-1,2,4-benzothiadiazine 1,1-dioxide The expected product is obtained according to the process described in Step D of Example 1.
Melting point: 230-232° C.

EXAMPLE 16

6-cyano-4-cyclopropyl-3,4-dihydro-2H-1,2,4-benzothiadiazine 1,1-dioxide

Step A: 4-cyano-2-fluorobenzenesulphonamide

The expected product is obtained according to the process described in Step A of Example 1, starting from 4-cyano-2-fluoroaniline.

Melting point: 149-152° C.

Step B: 4-cyano-2-cyclopropylaminobenzenesulphonamide

The expected product is obtained according to the process described in Step B of Example 1.

Step C: 6-cyano-4-cyclopropyl-4H-1,2,4-benzothiadiazine 1,1-dioxide

The expected product is obtained according to the process described in Step C of Example 1 (heating time: 24 hours, at 130° C.).

Melting point: 273-276° C.

Step D: 6-cyano-4-cyclopropyl-3,4-dihydro-2H-1,2,4-benzothiadiazine 1,1-dioxide

The expected product is obtained according to the process described in Step D of Example 1.

Melting point: 178-180° C.

EXAMPLE 17

8-bromo-4-cyclopropyl-6-fluoro-3,4-dihydro-2H-1,2,4-benzothiadiazine 1,1-dioxide Step A: 2-bromo-4,6-difluorobenzenesulphonamide The expected product is obtained according to the process described in Step A of Example 1, starting from 2-bromo-4,6-difluoroaniline.

Melting point: 122-124° C.

Step B: 2-bromo-6-cyclopropylamino-4-fluorobenzenesulphonamide

The expected product is obtained according to the process described in Step B of Example 1.

Step C: 8-bromo-4-cyclopropyl-6-fluoro-4H-1,2,4-benzothiadiazine 1,1-dioxide

The expected product is obtained according to the process described in Step C of Example 1 (heating time: 3 hours, at 130° C.).

Melting point: 270-273° C.

Step D: 8-bromo-4-cyclopropyl-6-fluoro-3,4-dihydro-2H-1,2,4-benzothiadiazine 1,1-dioxide The expected product is obtained according to the process described in Step D of Example 1.

Melting point: 197-199° C.

EXAMPLE 18

4-cyclopropyl-8-trifluoromethyl-3,4-dihydro-2H-1,2,4-benzothiadiazine 1,1-dioxide Step A: 2-fluoro-6-trifluoromethylbenzenesulphonamide The expected product is obtained according to the process described in Step A of Example 1, starting from 2-fluoro-6-trifluoromethylaniline.

Melting point: 114-118° C.

Step B: 2-cyclopropylamino-6-trifluoromethylbenzenesulphonamide

The expected product is obtained according to the process described in Step B of Example 1.

Step C: 4-cyclopropyl-8-trifluoromethyl-4H-1,2,4-benzothiadiazine 1,1-dioxide

The expected product is obtained according to the process described in Step C of Example 1 (heating time: 10 hours, at 130° C.).

Melting point: 195-197° C.

Step D: 4-cyclopropyl-8-trifluoromethyl-3,4-dihydro-2H-1,2,4-benzothiadiazine 1,1-dioxide The expected product is obtained according to the process described in Step D of Example 1.

Melting point: 239-241° C.

EXAMPLE 19

5-chloro-4-cyclopropyl-3,4-dihydro-2H-1,2,4-benzothiadiazine 1,1-dioxide

Step A: 3-chloro-2-fluorobenzenesulphonamide

The expected product is obtained according to the process described in Step A of Example 1, starting from 3-chloro-2-fluoroaniline.

Melting point: 149-153° C.

Step B: 3-chloro-2-cyclopropylaminobenzenesulphonamide

The expected product is obtained according to the process described in Step B of Example 1.

Step C: 5-chloro-4-cyclopropyl-4H-1,2,4-benzothiadiazine 1,1-dioxide

The expected product is obtained according to the process described in Step C of Example 1 (heating time: 24 hours, at 130° C.).

Melting point: 159-160° C.

Step D: 5-chloro-4-cyclopropyl-3,4-dihydro-2H-1,2,
4-benzothiadiazine 1,1-dioxide The expected product is obtained according to the process described in Step D of Example 1.
Melting point: 142-143° C.

EXAMPLE 20

8-bromo-6-chloro-4-cyclopropyl-3,4-dihydro-2H-1,
2,4-benzothiadiazine 1,1-dioxide Step A:
2-bromo-4-chloro-6-fluorobenzenesulphonamide The expected product is obtained according to the process described in Step A of Example 1, starting from 2-bromo-4-chloro-6-fluoroaniline.
Melting point: 122-126° C.

Step B: 2-bromo-4-chloro-6-cyclopropylaminobenzenesulphonamide

The expected product is obtained according to the process described in Step B of Example 1.

Step C: 8-bromo-6-chloro-4-cyclopropyl-4H-1,2,4-benzothiadiazine 1,1-dioxide

The expected product is obtained according to the process described in Step C of Example 1 (heating time: 3 hours).

Step D: 8-bromo-6-chloro-4-cyclopropyl-3,4-dihydro-2H-1,2,4-benzothiadiazine 1,1-dioxide The expected product is obtained according to the process described in Step D of Example 1.
Melting point: 177-180° C.

EXAMPLE 21

4-cyclopropyl-5-fluoro-3,4-dihydro-2H-1,2,4-benzothiadiazine 1,1-dioxide

Step A: 2,3-difluorobenzenesulphonamide

The expected product is obtained according to the process described in Step A of Example 1, starting from 2,3-difluoroaniline.
Melting point: 151-153° C.

Step B:
2-cyclopropylamino-3-fluorobenzenesulphonamide

The expected product is obtained according to the process described in Step B of Example 1.

Step C:
4-cyclopropyl-5-fluoro-4H-1,2,4-benzothiadiazine
1,1-dioxide

The expected product is obtained according to the process described in Step C of Example 1 (heating time: 48 hours).
Melting point: 151-152° C.

Step D: 4-cyclopropyl-5-fluoro-3,4-dihydro-2H-1,2,
4-benzothiadiazine 1,1-dioxide The expected product is obtained according to the process described in Step D of Example 1.
Melting point: 161-163° C.

EXAMPLE 22

6-bromo-4-cyclopropyl-3,4-dihydro-7-methyl-2H-1,
2,4-benzothiadiazine 1,1-dioxide Step A:
4-bromo-2-fluoro-5-methylbenzenesulphonamide The expected product is obtained according to the process described in Step A of Example 1, starting from 4-bromo-2-fluoro-5-methylaniline.
Melting point: 124-125° C.

Step B: 4-bromo-2-cyclopropylamino-5-methylbenzenesulphonamide

The expected product is obtained according to the process described in Step B of Example 1.

Step C: 6-bromo-4-cyclopropyl-7-methyl-4H-1,2,4-benzothiadiazine 1,1-dioxide

The expected product is obtained according to the process described in Step C of Example 1 (heating time: 24 hours).
Melting point: 219-220° C.

Step D: 6-bromo-4-cyclopropyl-3,4-dihydro-7-methyl-2H-1,2,4-benzothiadiazine 1,1-dioxide The expected product is obtained according to the process described in Step D of Example 1.
Melting point: 199-200° C.

EXAMPLE 23

5,6-dichloro-4-cyclopropyl-3,4-dihydro-2H-1,2,4-benzothiadiazine 1,1-dioxide

Step A: 3,4-dichloro-2-fluorobenzenesulphonamide

The expected product is obtained according to the process described in Step A of Example 1, starting from 3,4-dichloro-2-fluoroaniline.

Step B:
3,4-dichloro-2-cyclopropylaminobenzenesulphonamide

The expected product is obtained according to the process described in Step B of Example 1.

Step C: 5,6-dichloro-4-cyclopropyl-4H-1,2,4-benzothiadiazine 1,1-dioxide

The expected product is obtained according to the process described in Step C of Example 1 (heating time: 2 hours, at 130° C.).
Melting point: 183-185° C.

Step D: 5,6-dichloro-4-cyclopropyl-3,4-dihydro-2H-
1,2,4-benzothiadiazine 1,1-dioxide The expected product is obtained according to the process described in Step D of Example 1.
Melting point: 132-133° C.

EXAMPLE 24

8-bromo-4-cyclopropyl-3,4-dihydro-2H-1,2,4-benzothiadiazine 1,1-dioxide

Step A: 2-bromo-6-fluorobenzenesulphonamide

The expected product is obtained according to the process described in Step A of Example 1, starting from 2-bromo-6-fluoroaniline.
Melting point: 185-187° C.

Step B: 2-bromo-6-cyclopropylaminobenzenesulphonamide

The expected product is obtained according to the process described in Step B of Example 1.

Step C: 8-bromo-4-cyclopropyl-4H-1,2,4-benzothiadiazine 1,1-dioxide

The expected product is obtained according to the process described in Step C of Example 1 (heating time: 1.5 hours).

Step D: 8-bromo-4-cyclopropyl-3,4-dihydro-2H-1,2,4-benzothiadiazine 1,1-dioxide

The expected product is obtained according to the process described in Step D of Example 1.
Melting point: 189-191° C.

EXAMPLE 25

4-cyclopropyl-5,7-difluoro-3,4-dihydro-2H-1,2,4-benzothiadiazine 1,1-dioxide

Step A: 2,3,5-trifluorobenzenesulphonamide

The expected product is obtained according to the process described in Step A of Example 1, starting from 2,3,5-trifluoroaniline.
Melting point: 115-117° C.

Step B: 2-cyclopropylamino-3,5-difluorobenzenesulphonamide

The expected product is obtained according to the process described in Step B of Example 1 (heating time: 40 hours).

Step C: 4-cyclopropyl-5,7-difluoro-4H-1,2,4-benzothiadiazine 1,1-dioxide

The expected product is obtained according to the process described in Step C of Example 1 (heating time: 3 hours, at 130° C.).
Melting point: 160-163° C.

Step D: 4-cyclopropyl-5,7-difluoro-3,4-dihydro-2H-1,2,4-benzothiadiazine 1,1-dioxide The expected product is obtained according to the process described in Step D of Example 1.
Melting point: 149-151° C.

EXAMPLE 26

4-cyclopropyl-5-fluoro-3,4-dihydro-6-methyl-2H-1,2,4-benzothiadiazine 1,1-dioxide Step A: 2,3-difluoro-4-methylbenzenesulphonamide The expected product is obtained according to the process described in Step A of Example 1, starting from 2,3-difluoro-4-methylaniline.
Melting point: 171-173° C.

Step B: 2-cyclopropylamino-3-fluoro-4-methylbenzenesulphonamide

The expected product is obtained according to the process described in Step B of Example 1.

Step C: 4-cyclopropyl-5-fluoro-6-methyl-4H-1,2,4-benzothiadiazine 1,1-dioxide

The expected product is obtained according to the process described in Step C of Example 1 (heating time: 24 hours, at 130° C.).
Melting point: 189-192° C.

Step D: 4-cyclopropyl-5-fluoro-3,4-dihydro-6-methyl-2H-1,2,4-benzothiadiazine 1,1-dioxide The expected product is obtained according to the process described in Step D of Example 1.
Melting point: 135-138° C.

EXAMPLE 27

8-chloro-4-cyclopropyl-7-fluoro-3,4-dihydro-2H-1,2,4-benzothiadiazine 1,1-dioxide Step A: 2-chloro-3,6-difluorobenzenesulphonamide The expected product is obtained according to the process described in Step A of Example 1, starting from 2-chloro-3,6-difluoroaniline.
Melting point: 175-178° C.

Step B: 2-chloro-6-cyclopropylamino-3-fluorobenzenesulphonamide

The expected product is obtained according to the process described in Step B of Example 1.

Step C: 8-chloro-4-cyclopropyl-7-fluoro-4H-1,2,4-benzothiadiazine 1,1-dioxide

The expected product is obtained according to the process described in Step C of Example 1 (heating time: 24 hours, at 130° C.).
Melting point: 260-263° C.

Step D: 8-chloro-4-cyclopropyl-7-fluoro-3,4-dihydro-2H-1,2,4-benzothiadiazine 1,1-dioxide The expected product is obtained according to the process described in Step D of Example 1.
Melting point: 198-200° C.

EXAMPLE 28

4-cyclopropyl-3,4-dihydro-6-iodo-2H-1,2,4-benzothiadiazine 1,1-dioxide

Step A: 2-fluoro-4-iodobenzenesulphonamide

The expected product is obtained according to the process described in Step A of Example 1, starting from 2-fluoro-4-iodoaniline.

Step B: 2-cyclopropylamino-4-iodobenzenesulphonamide

The expected product is obtained according to the process described in Step B of Example 1.

Step C: 4-cyclopropyl-6-iodo-4H-1,2,4-benzothiadiazine 1,1-dioxide

The expected product is obtained according to the process described in Step C of Example 1 (heating time: 24 hours, at 130° C.).
Melting point: 304-307° C.

Step D: 4-cyclopropyl-3,4-dihydro-6-iodo-2H-1,2,4-benzothiadiazine 1,1-dioxide

The expected product is obtained according to the process described in Step D of Example 1.
Melting point: 183-185° C.

EXAMPLE 29

4-cyclopropyl-8-fluoro-3,4-dihydro-2H-1,2,4-benzothiadiazine 1,1-dioxide

Step A: 2-cyclopropylamino-6-fluorobenzenesulphonamide

The expected product is obtained according to the process described in Step B of Example 1, starting from commercial 2,6-difluorobenzenesulphonamide.

Step B: 4-cyclopropyl-8-fluoro-4H-1,2,4-benzothiadiazine 1,1-dioxide

The expected product is obtained according to the process described in Step C of Example 5 (heating time: 24 hours).
Melting point: 156-157° C.

Step C: 4-cyclopropyl-8-fluoro-3,4-dihydro-2H-1,2,4-benzothiadiazine 1,1-dioxide The expected product is obtained according to the process described in Step D of Example 1.
Melting point: 177-179° C.

EXAMPLE 30

6,8-dibromo-4-cyclopropyl-3,4-dihydro-2H-1,2,4-benzothiadiazine 1,1-dioxide

Step A: 2,4-dibromo-6-fluorobenzenesulphonamide

The expected product is obtained according to the process described in Step A of Example 1, starting from 2,4-dibromo-6-fluoroaniline.
Melting point: 153-157° C.

Step B: 2,4-dibromo-6-cyclopropylaminobenzenesulphonamide

The expected product is obtained according to the process described in Step B of Example 1.

Step C: 6,8-dibromo-4-cyclopropyl-4H-1,2,4-benzothiadiazine 1,1-dioxide

The expected product is obtained according to the process described in Step C of Example 1.
Melting point: 254-256° C.

Step D: 6,8-dibromo-4-cyclopropyl-3,4-dihydro-2H-1,2,4-benzothiadiazine 1,1-dioxide The expected product is obtained according to the process described in Step D of Example 1.
Melting point: 203-205° C.

EXAMPLE 31

5-chloro-4-cyclopropyl-6-fluoro-3,4-dihydro-2H-1,2,4-benzothiadiazine 1,1-dioxide Step A: 3-chloro-2,4-difluorobenzenesulphonamide The expected product is obtained according to the process described in Step A of Example 1, starting from 3-chloro-2,4-difluoroaniline.
Melting point: 128-132° C.

Step B: 3-chloro-2-cyclopropylamino-4-fluorobenzenesulphonamide

The expected product is obtained according to the process described in Step B of Example 1.

Step C: 5-chloro-4-cyclopropyl-6-fluoro-4H-1,2,4-benzothiadiazine 1,1-dioxide

The expected product is obtained according to the process described in Step C of Example 1 (heating time: 2 hours, at 130° C.).
Melting point: 147-148° C.

Step D: 5-chloro-4-cyclopropyl-6-fluoro-3,4-dihydro-2H-1,2,4-benzothiadiazine 1,1-dioxide The expected product is obtained according to the process described in Step D of Example 1.
Melting point: 141-143° C.

EXAMPLE 32

8-chloro-4-cyclopropyl-3,4-dihydro-2H-1,2,4-benzothiadiazine 1,1-dioxide

Step A: 2-chloro-6-fluorobenzenesuilphonamide

The expected product is obtained according to the process described in Step A of Example 1, starting from 2-chloro-6-fluoroaniline.
Melting point: 187-190° C.

Step B: 2-chloro-6-cyclopropylaminobenzenesulphonamide

The expected product is obtained according to the process described in Step B of Example 1.

Step C: 8-chloro-4-cyclopropyl-4H-1,2,4-benzothiadiazine 1,1-dioxide

The expected product is obtained according to the process described in Step C of Example 1 (heating time: 2 hours, at 130° C.).
Melting point: 207-209° C.

Step D: 8-chloro-4-cyclopropyl-3,4-dihydro-2H-1,2,4-benzothiadiazine 1,1-dioxide The expected product is obtained according to the process described in Step D of Example 1.
Melting point: 182-184° C.

EXAMPLE 33

6-bromo-4-cyclopropyl-8-trifluoromethyl-3,4-dihydro-2H-1,2,4-benzothiadiazine 1,1-dioxide Step A: 4-bromo-2-fluoro-6-trifluoromethylbenzenesulphonamide The expected product is obtained according to the process described in Step A of Example 1, starting from 4-bromo-2-fluoro-6-trifluoromethylaniline.
Melting point: 133-135° C.

Step B: 4-bromo-2-cyclopropylamino-6-trifluoromethylbenzenesulphonamide

The expected product is obtained according to the process described in Step B of Example 1.

Step C: 6-bromo-4-cyclopropyl-8-trifluoromethyl-4H-1,2,4-benzothiadiazine 1,1-dioxide The expected product is obtained according to the process described in Step C of Example 1 (heating time: 6 hours).
Melting point: 253-254° C.

Step D: 6-bromo-4-cyclopropyl-8-trifluoromethyl-3,4-dihydro-2H-1,2,4-benzothiadiazine 1,1-dioxide The expected product is obtained according to the process described in Step D of Example 1.
Melting point: 200-201° C.

EXAMPLE 34

6-bromo-4-cyclopropyl-7-fluoro-3,4-dihydro-2H-1,2,4-benzothiadiazine 1,1-dioxide Step A: 4-bromo-2,5-difluorobenzenesulphonamide The expected product is obtained according to the process described in Step A of Example 1, starting from 4-bromo-2,5-difluoroaniline.
Melting point: 159-163° C.

Step B: 4-bromo-2-cyclopropylamino-5-fluorobenzenesulphonamide

The expected product is obtained according to the process described in Step B of Example 1.

Step C: 6-bromo-4-cyclopropyl-7-fluoro-4H-1,2,4-benzothiadiazine 1,1-dioxide

The expected product is obtained according to the process described in Step C of Example 1 (heating time: 24 hours).
Melting point: 218-219° C.

Step D: 6-bromo-4-cyclopropyl-7-fluoro-3,4-dihydro-2H-1,2,4-benzothiadiazine 1,1-dioxide The expected product is obtained according to the process described in Step D of Example 1.
Melting point: 163-165° C.

EXAMPLE 35

6-bromo-4-cyclopropyl-3,4-dihydro-2H-1,2,4-benzothiadiazine 1,1-dioxide

Step A: 4-bromo-2-cyclopropylaminobenzenesulphonamide

The expected product is obtained according to the process described in Step B of Example 1, starting from commercial 4-bromo-2-fluorobenzenesulphonamide.

Step B: 6-bromo-4-cyclopropyl-4H-1,2,4-benzothiadiazine 1,1-dioxide

The expected product is obtained according to the process described in Step C of Example 1 (heating time: 24 hours, at 130° C.).
Melting point: 268-271° C.

Step C: 6-bromo-4-cyclopropyl-3,4-dihydro-2H-1,2,4-benzothiadiazine 1,1-dioxide

The expected product is obtained according to the process described in Step D of Example 1.
Melting point: 180-181° C.

EXAMPLE 36

8-chloro-4-cyclopropyl-3,4-dihydro-5-methyl-2H-1,2,4-benzothiadiazine 1,1-dioxide Step A: 6-chloro-2-fluoro-3-methylbenzenesulphonamide The expected product is obtained according to the process described in Step A of Example 1, starting from 6-chloro-2-fluoro-3-methylaniline.
Melting point: 174-176° C.

Step B: 6-chloro-2-cyclopropylamino-3-methylbenzenesulphonamide

The expected product is obtained according to the process described in Step B of Example 1 (heating time: 48 hours).

Step C: 8-chloro-4-cyclopropyl-5-methyl-4H-1,2,4-benzothiadiazine 1,1-dioxide

The expected product is obtained according to the process described in Step C of Example 1.

Step D: 8-chloro-4-cyclopropyl-3,4-dihydro-5-methyl-2H-1,2,4-benzothiadiazine 1,1-dioxide The expected product is obtained according to the process described in Step D of Example 1.
Melting point: 215-217° C.

EXAMPLE 37

4-cyclopropyl-3,4-dihydro-6-methyl-2H-1,2,4-benzothiadiazine 1,1-dioxide

Step A: 2-fluoro-4-methylbenzenesulphonamide

The expected product is obtained according to the process described in Step A of Example 1, starting from 2-fluoro-4-methylaniline.
Melting point: 136-137° C.

Step B: 2-cyclopropylamino-4-methylbenzenesulphonamide

The expected product is obtained according to the process described in Step B of Example 1 (heating time: 24 hours).

Step C: 4-cyclopropyl-6-methyl-4H-1,2,4-benzothiadiazine 1,1-dioxide

The expected product is obtained according to the process described in Step C of Example 1.
Melting point: 224-226° C.

Step D: 4-cyclopropyl-3,4-dihydro-6-methyl-2H-1,2,4-benzothiadiazine 1,1-dioxide The expected product is obtained according to the process described in Step D of Example 1.
Melting point: 157-158° C.

EXAMPLE 38

4-cyclopropyl-6,8-difluoro-3,4-dihydro-2H-1,2,4-benzothiadiazine 1,1-dioxide Step A: 2,4,6-trifluorobenzenesulphonamide The expected product is obtained according to the process described in Step A of Example 1, starting from 2,4,6-trifluoroaniline.
Melting point: 102-106° C.

Step B: 2-cyclopropylamino-4,6-difluorobenzenesulphonamide

The expected product is obtained according to the process described in Step B of Example 1.

Step C: 4-cyclopropyl-6,8-difluoro-4H-1,2,4-benzothiadiazine 1,1-dioxide

The expected product is obtained according to the process described in Step C of Example 1 (heating time: 24 hours).
Melting point: 167-168° C.

Step D: 4-cyclopropyl-6,8-difluoro-3,4-dihydro-2H-1,2,4-benzothiadiazine 1,1-dioxide The expected product is obtained according to the process described in Step D of Example 1.
Melting point: 161-164° C.

EXAMPLE 39

4-cyclopropyl-5,6-difluoro-3,4-dihydro-2H-1,2,4-benzothiadiazine 1,1-dioxide Step A: 2,3,4-trifluorobenzenesulphonamide The expected product is obtained according to the process described in Step A of Example 1, starting from 2,3,4-trifluoroaniline.
Melting point: 111-114° C.

Step B: 2-cyclopropylamino-3,4-difluorobenzenesulphonamide

The expected product is obtained according to the process described in Step B of Example 1.

Step C: 4-cyclopropyl-5,6-difluoro-4H-1,2,4-benzothiadiazine 1,1-dioxide

The expected product is obtained according to the process described in Step C of Example 1 (heating time: 6 hours).
Melting point: 182-184° C.

Step D: 4-cyclopropyl-5,6-difluoro-3,4-dihydro-2H-1,2,4-benzothiadiazine 1,1-dioxide The expected product is obtained according to the process described in Step D of Example 1.
Melting point: 160-162° C.

EXAMPLE 40

7-bromo-4-cyclopropyl-3,4-dihydro-2H-1,2,4-benzothiadiazine 1,1-dioxide

Step A: 5-bromo-2-fluorobenzenesulphonamide

The expected product is obtained according to the process described in Step A of Example 1, starting from 5-bromo-2-fluoroaniline.
Melting point: 149-151° C.

Step B: 5-bromo-2-cyclopropylaminobenzenesulphonamide

The expected product is obtained according to the process described in Step B of Example 1.

Step C: 7-bromo-4-cyclopropyl-4H-1,2,4-benzothiadiazine 1,1-dioxide

The expected product is obtained according to the process described in Step C of Example 1 (heating time: 5 hours, at 130° C.).
Melting point: 242-244° C.

Step D: 7-bromo-4-cyclopropyl-3,4-dihydro-2H-1,2,4-benzothiadiazine 1,1-dioxide

The expected product is obtained according to the process described in Step D of Example 1.
Melting point: 178-179° C.

EXAMPLE 41

4-cyclopropyl-3,4-dihydro-7-nitro-2H-1,2,4-benzothiadiazine 1,1-dioxide

Step A: 2-chloro-5-nitrobenzenesulphonamide

A portion of glacial acetic acid (160 mL) is saturated for 30 minutes with gaseous sulphur dioxide. To the resulting solution, cooled on an ice bath, there is added an aqueous solution of $CuCl_2$ (7 g in 20 mL), with stirring (suspension A).
2-Chloro-5-nitroaniline (15 g) is dissolved in a mixture of glacial acetic acid (160 mL) and concentrated HCl (40 mL). To the resulting solution, cooled in a bath of ice and salt (−5° C.), there is added dropwise an aqueous solution of $NaNO_2$ (8 g in 20 mL), with stirring. At the end of the addition, the resulting solution is slowly mixed with suspension A, with stirring. After stirring for 15 minutes, the suspension is poured onto ice (400 g). The precipitate that is formed is collected by filtration, washed with water and immediately re-dissolved in dioxane (150 mL). The solution obtained is added gradually, with stirring, to a concentrated ammonium hydroxide solution (300 mL) previously cooled on an ice bath. After stirring for 30 minutes, the organic solvent and some of the ammonia are removed by evaporation under reduced pressure. The aqueous solution/suspension obtained is adjusted to neutral pH by adding 6N HCl. The precipitate formed is collected by filtration and washed with water. It is suspended in water (200 mL), and 10% NaOH is added until the pH is clearly alkaline. The suspension is heated in order to facilitate dissolution of the title product. The insoluble material that remains is removed by filtration in the hot state. The cooled filtrate is adjusted to neutral or slightly acid pH by adding 6N HCl. The precipitate is collected on a filter, washed with water and dried.
Melting point: 180-183° C.

Step B: 2-cyclopropylamino-5-nitrobenzenesulphonamide

2-Chloro-5-nitrobenzenesulphonamide (5 g) prepared in the Step above is introduced into a hermetically closed vessel containing a mixture of dioxane (70 mL) and cyclopropylamine (3.5 mL). The hermetically closed vessel is placed in an oven at 100° C. for 24 hours. After this time period, the solvent and the reagent are removed by concentrating under reduced pressure. The residue is taken up in methanol (20 mL) and the insoluble material, which contains the title product, is collected by filtration, washed with methanol and dried.

Step C: 4-cyclopropyl-7-nitro-4H-1,2,4-benzothiadiazine 1,1-dioxide

In a round-bottom flask, a mixture of 2-cyclopropylamino-5-nitrobenzenesulphonamide (5 g), originating from the Step above, and ethyl orthoformate (50 mL) is heated in the open state at 130° C. for 3 hours. The suspension obtained is cooled on an ice bath and the insoluble material is collected by filtration, washed with ether and dried.
Melting point: 233-235° C.

Step D: 4-cyclopropyl-3,4-dihydro-7-nitro-2H-1,2,4-benzothiadiazine 1,1-dioxide

The expected product is obtained according to the process described in Step D of Example 1.
Melting point: 198-201° C.

EXAMPLE 42

7-acetamido-4-cyclopropyl-3,4-dihydro-2H-1,2,4-benzothiadiazine 1,1-dioxide

Step A: 7-amino-4-cyclopropyl-4H-1,2,4-benzothiadiazine 1,1-dioxide

To a solution of 4-cyclopropyl-7-nitro-4H-1,2,4-benzothiadiazine 1,1-dioxide (5 g; prepared in Step C of Example 41) in ethanol (180 mL) there is added 10 % palladium-on-carbon (500 mg). The suspension is placed in a hydrogenator under 10 atmospheres of $H_2$ for 30 minutes at ambient temperature. The suspension is concentrated to dryness under reduced pressure and the residue is taken up in boiling acetone (300 mL). The insoluble material is removed by filtration in the hot state and is washed with boiling acetone. The filtrate is concentrated to dryness and the residue is recrystallised from methanol.
Melting point: 283-285° C.

Step B: 7-acetamido-4-cyclopropyl-3,4-dihydro-2H-1,2,4-benzothiadiazine 1,1-dioxide Acetyl chloride (0.5 mL) is added to a solution of 7-amino-4-cyclopropyl-4H-1,2,4-benzothiadiazine 1,1-dioxide (0.5 g), prepared in the Step above, in dioxane (20 mL) and stirring is carried out at ambient temperature for 16 hours. After removing the solvent by distillation under reduced pressure, the residue is taken up in water, and the precipitate, of 7-acetamido-4-cyclopropyl-4H-1,2,4-benzothiadiazine 1,1-dioxide, is collected by filtration, washed with water and dried. It is used directly in a subsequent step, according to the procedure described in Step D of Example 1, in order to obtain the expected product.

Melting point: 230-232° C.

EXAMPLE 43

6,7-dichloro-4-cyclobutyl-3,4-dihydro-2H-1,2,4-benzothiadiazine 1,1-dioxide

Step A:
4,5-dichloro-2-cyclobutylaminobenzenesulphonamide

Starting from 4,5-dichloro-2-fluoroaniline, the expected product is obtained according to the process described in Steps A and B of Example 1, with addition of cyclobutylamine in Step B.

Step B: 6,7-dichloro-4-cyclobutyl-4H-1,2,4-benzothiadiazine 1,1-dioxide

The expected product is obtained according to the process described in Step C of Example 1 (heating time: 24 hours).
Melting point: 238-240° C.

Step C: 6,7-dichloro-4-cyclobutyl-3,4-dihydro-2H-1,2,4-benzothiadiazine 1,1-dioxide The expected product is obtained according to the process described in Step D of Example 1.
Melting point: 161-163° C.

EXAMPLE 44

7-chloro-4-cyclobutyl-3,4-dihydro-2H-1,2,4-benzothiadiazine 1,1-dioxide

Step A:
4-cyclobutyl-7-nitro-4H-1,2,4-benzothiadiazine 1,1-dioxide

Starting from 2-chloro-5-nitroaniline, the expected product is obtained according to the process described in Steps A, B and C of Example 41, with addition of cyclobutylamine in Step B.
Melting point: 229-232° C.

Step B:
7-amino-4-cyclobutyl-4H-1,2,4-benzothiadiazine 1,1-dioxide

The expected product is obtained according to the process described in Step A of Example 42.
Melting point: 278-280° C.

Step C:
7-chloro-4-cyclobutyl-4H-1,2,4-benzothiadiazine 1,1-dioxide

A solution of $CuSO_4.5H_2O$ (84 g) and NaCl (22.5 g) in water (200 mL) is cooled on an ice bath, and an aqueous solution of $Na_2S_2O_5$ (22.5 g in 100 mL) is added dropwise. After stirring for 15 minutes, the precipitate, of $Cu_2Cl_2$, is collected by filtration and washed with water.

A solution of 7-amino-4-cyclobutyl-4H-1,2,4-benzothiadiazine 1,1-dioxide prepared in the Step above (3.48 g) in 6N HCl (40 mL) is cooled on an ice bath and then an aqueous solution of $NaNO_2$ (2 g in 15 mL) is added dropwise. The solution obtained is added gradually to a solution of the $Cu_2Cl_2$ in concentrated HCl (30 mL). After stirring for 30 minutes at ambient temperature, water (150 mL) is added to the reaction mixture and the precipitate obtained is collected by filtration, washed with water and dried.

Melting point: 229-231° C.

Step D: 7-chloro-4-cyclobutyl-3,4-dihydro-2H-1,2,4-benzothiadiazine 1,1-dioxide

To a solution of the 7-chloro-4-cyclobutyl-4H-1,2,4-benzothiadiazine 1,1-dioxide originating from the Step above (3 g) in isopropanol (100 mL) there is added finely ground $NaBH_4$ (2.5 g) and then heating is carried out for 10 minutes at 55° C. The solvent is removed by evaporation under reduced pressure. The residue is taken up in water (100 mL) and brought to acid pH by adding 6N HCl. The title product is extracted with chloroform (3×50 mL). The organic phase is dried over $MgSO_4$ and filtered. The filtrate is evaporated to dryness and the residue is purified by chromatography on a silica column (mobile phase: chloroform). The product obtained is recrystallised from methanol.

Melting point: 162-164° C.

EXAMPLE 45

6-chloro-4-cyclobutyl-3,4-dihydro-2H-1,2,4-benzothiadiazine 1,1-dioxide

Step A:
4-chloro-2-cyclobutylaminobenzenesulphonamide

Starting from 4-chloro-2-fluoroaniline, the expected product is obtained according to the process described in Steps A and B of Example 1, with addition of cyclobutylamine in Step B.

Step B:
6-chloro-4-cyclobutyl-4H-1,2,4-benzothiadiazine 1,1-dioxide

The expected product is obtained according to the process described in Step C of Example 1 (heating time: 6 hours, at 130° C.).
Melting point: 224-226° C.

Step C: 6-chloro-4-cyclobutyl-3,4-dihydro-2H-1,2,4-benzothiadiazine 1,1-dioxide

The expected product is obtained according to the process described in Step D of Example 1.
Melting point: 183-185° C.

EXAMPLE 46

4-cyclobutyl-3,4-dihydro-7-nitro-2H-1,2,4-benzothiadiazine 1,1-dioxide

Starting from 4-cyclobutyl-7-nitro-4H-1,2,4-benzothiadiazine 1,1-dioxide (prepared in Step A of Example 44), the expected product is obtained according to the process described in Step D of Example 1.
Melting point: 188-190° C.

EXAMPLE 47

6,7-dichloro-4-cyclopentyl-3,4-dihydro-2H-1,2,4-benzothiadiazine 1,1-dioxide

Step A:
4,5-dichloro-2-cyclopentylaminobenzenesulphonamide

Starting from 4,5-dichloro-2-fluoroaniline, the expected product is obtained according to the process described in Steps A and B of Example 1, with addition of cyclopentylamine in Step B.

Step B: 6,7-dichloro-4-cyclopentyl-4H-1,2,4-benzothiadiazine 1,1-dioxide

The expected product is obtained according to the process described in Step C of Example 5 (heating time: 72 hours, at 140° C.).
Melting point: 189-191° C.

Step C: 6,7-dichloro-4-cyclopentyl-3,4-dihydro-2H-1,2,4-benzothiadiazine 1,1-dioxide The expected product is obtained according to the process described in Step D of Example 1.
Melting point: 221-224° C.

EXAMPLE 48

7-chloro-4-cyclopentyl-3,4-dihydro-2H-1,2,4-benzothiadiazine 1,1-dioxide

Step A:
5-chloro-2-cyclopentylaminobenzenesulphonamide

Starting from 5-chloro-2-fluoroaniline, the expected product is obtained according to the process described in Steps A and B of Example 1, with addition of cyclopentylamine in Step B.

Step B:
7-chloro-4-cyclopentyl-4H-1,2,4-benzothiadiazine 1,1-dioxide

The expected product is obtained according to the process described in Step C of Example 5 (heating time: 96 hours).
Melting point: 218-220° C.

Step C: 7-chloro-4-cyclopentyl-3,4-dihydro-2H-1,2,4-benzothiadiazine 1,1-dioxide The expected product is obtained according to the process described in Step D of Example 1.
Melting point: 193-194° C.

EXAMPLE 49

6-chloro-4-cyclopentyl-3,4-dihydro-2H-1,2,4-benzothiadiazine 1,1-dioxide

Step A:
4-chloro-2-cyclopentylaminobenzenesulphonamide

Starting from 4-chloro-2-fluoroaniline, the expected product is obtained according to the process described in Steps A and B of Example 1, with addition of cyclopentylamine in Step B.

Step B:
6-chloro-4-cyclopentyl-4H-1,2,4-benzothiadiazine 1,1-dioxide

The expected product is obtained according to the process described in Step C of Example 5.
Melting point: 170-172° C.

Step C: 6-chloro-4-cyclopentyl-3,4-dihydro-2H-1,2,4-benzothiadiazine 1,1-dioxide The expected product is obtained according to the process described in Step D of Example 1.
Melting point: 175-177° C.

EXAMPLE 50

6,7-dichloro-4-cyclohexyl-3,4-dihydro-2H-1,2,4-benzothiadiazine 1,1-dioxide

Step A:
4,5-dichloro-2-cyclohexylaminobenzenesulphonamide

Starting from 4,5-dichloro-2-fluoroaniline, the expected product is obtained according to the process described in Steps A and B of Example 1, with addition of cyclohexylamine in Step B which is heated at 80° C. in a hermetically closed vessel for 72 hours.

Step B: 6,7-dichloro-4-cyclohexyl-4H-1,2,4-benzothiadiazine 1,1-dioxide

The expected product is obtained according to the process described in Step C of Example 5 (heating time: 72 hours, at 140° C.).
Melting point: 219-222° C.

Step C: 6,7-dichloro-4-cyclohexyl-3,4-dihydro-2H-1,2,4-benzothiadiazine 1,1-dioxide The expected product is obtained according to the process described in Step D of Example 1.
Melting point: 207-209° C.

EXAMPLE 51

7-chloro-4-cyclohexyl-3,4-dihydro-2H-1,2,4-benzothiadiazine 1,1-dioxide

Step A:
5-chloro-2-cyclohexylaminobenzenesulphonamide

Starting from 5-chloro-2-fluoroaniline, the expected product is obtained according to the process described in Steps A and B of Example 1, with addition of cyclohexylamine in Step B.

Step B:
7-chloro-4-cyclohexyl-4H-1,2,4-benzothiadiazine 1,1-dioxide

The expected product is obtained according to the process described in Step C of Example 1 (heating time: 5 hours, at 130° C.).
Melting point: 209-211° C.

Step C: 7-chloro-4-cyclohexyl-3,4-dihydro-2H-1,2,4-benzothiadiazine 1,1-dioxide

The expected product is obtained according to the process described in Step D of Example 1.
Melting point: 233-235° C.

EXAMPLE 52

6-chloro-4-cyclohexyl-3,4-dihydro-2H-1,2,4-benzothiadiazine 1,1-dioxide

Step A:
4-chloro-2-cyclohexylaminobenzenesulphonamide

Starting from 4-chloro-2-fluoroaniline, the expected product is obtained according to the process described in Steps A and B of Example 1, with addition of cyclohexylamine in Step B.

Step B:
6-chloro-4-cyclohexyl-4H-1,2,4-benzothiadiazine 1,1-dioxide

The expected product is obtained according to the process described in Step C of Example 1 (heating time: 48 hours, at 130° C.).
Melting point: 189-191° C.

Step C: 6-chloro-4-cyclohexyl-3,4-dihydro-2H-1,2,4-benzothiadiazine 1,1-dioxide

The expected product is obtained according to the process described in Step D of Example 1.
Melting point: 178-180° C.

EXAMPLE 53

6,7-dichloro-4-cycloheptyl-3,4-dihydro-2H-1,2,4-benzothiadiazine 1,1-dioxide

Step A:
4,5-dichloro-2-cycloheptylaminobenzenesulphonamide

Starting from 4,5-dichloro-2-fluoroaniline, the expected product is obtained according to the process described in Steps A and B of Example 1, with addition of cycloheptylamine in Step B.

Step B: 6,7-dichloro-4-cycloheptyl-4H-1,2,4-benzothiadiazine 1,1-dioxide

The expected product is obtained according to the process described in Step C of Example 5 (heating time: 72 hours, at 140° C.).
Melting point: 222-224° C.

Step C: 6,7-dichloro-4-cycloheptyl-3,4-dihydro-2H-1,2,4-benzothiadiazine 1,1-dioxide The expected product is obtained according to the process described in Step D of Example 1.
Melting point: 191-192° C.

EXAMPLE 54

7-chloro-4-cycloheptyl-3,4-dihydro-2H-1,2,4-benzothiadiazine 1,1-dioxide

Step A:
5-chloro-2-cycloheptylaminobenzenesulphonamide

Starting from 5-chloro-2-fluoroaniline, the expected product is obtained according to the process described in Steps A and B of Example 1, with addition of cycloheptylamine in Step B.

Step B:
7-chloro-4-cycloheptyl-4H-1,2,4-benzothiadiazine 1,1-dioxide

The expected product is obtained according to the process described in Step C of Example 1 (heating time: 24 hours, at 130° C.).
Melting point: 241-243° C.

Step C: 7-chloro-4-cycloheptyl-3,4-dihydro-2H-1,2,4-benzothiadiazine 1,1-dioxide The expected product is obtained according to the process described in Step D of Example 1.
Melting point: 216-218° C.

EXAMPLE 55

6-chloro-4-cycloheptyl-3,4-dihydro-2H-1,2,4-benzothiadiazine 1,1-dioxide

Step A:
4-chloro-2-cycloheptylaminobenzenesulphonamide

Starting from 4-chloro-2-fluoroaniline, the expected product is obtained according to the process described in Steps A and B of Example 1, with addition of cycloheptylamine in Step B.

Step B:
6-chloro-4-cycloheptyl-4H-1,2,4-benzothiadiazine 1,1-dioxide

The expected product is obtained according to the process described in Step C of Example 1 (heating time: 72 hours, at 130° C.).
Melting point: 209-211° C.

Step C: 6-chloro-4-cycloheptyl-3,4-dihydro-2H-1,2,4-benzothiadiazine 1,1-dioxide The expected product is obtained according to the process described in Step D of Example 1.
Melting point: 149-151° C.

EXAMPLE 56

6,7-dichloro-4-cyclooctyl-3,4-dihydro-2H-1,2,4-benzothiadiazine 1,1-dioxide

Step A:
4,5-dichloro-2-cyclooctylaminobenzenesulphonamide

Starting from 4,5-dichloro-2-fluoroaniline, the expected product is obtained according to the process described in Steps A and B of Example 1, with addition of cyclooctylamine in Step B which is heated at 80° C. in a hermetically closed vessel for 72 hours.

Step B: 6,7-dichloro-4-cyclooctyl-4H-1,2,4-benzothiadiazine 1,1-dioxide

The expected product is obtained according to the process described in Step C of Example 5 (heating time: 72 hours, at 140° C.).
Melting point: 229-231° C.

Step C: 6,7-dichloro-4-cyclooctyl-3,4-dihydro-2H-1,2,4-benzothiadiazine 1,1-dioxide The expected product is obtained according to the process described in Step D of Example 1.
Melting point: 154-155° C.

EXAMPLE 57

7-chloro-4-cyclooctyl-3,4-dihydro-2H-1,2,4-benzothiadiazine 1,1-dioxide

Step A:
5-chloro-2-cyclooctylaminobenzenesulphonamide

Starting from 5-chloro-2-fluoroaniline, the expected product is obtained according to the process described in Steps A and B of Example 1, with addition of cyclooctylamine in Step B.

Step B:
7-chloro-4-cyclooctyl-4H-1,2,4-benzothiadiazine 1,1-dioxide

The expected product is obtained according to the process described in Step C of Example 1 (heating time: 24 hours, at 130° C.).
Melting point: 235-237° C.

Step C: 7-chloro-4-cyclooctyl-3,4-dihydro-2H-1,2,4-benzothiadiazine 1,1-dioxide

The expected product is obtained according to the process described in Step D of Example 1.
Melting point: 184-186° C.

EXAMPLE 58

6-chloro-4-cyclooctyl-3,4-dihydro-2H-1,2,4-benzothiadiazine 1,1-dioxide

Step A:
4-chloro-2-cyclooctylaminobenzenesulphonamide

Starting from 4-chloro-2-fluoroaniline, the expected product is obtained according to the process described in Steps A and B of Example 1, with addition of cyclooctylamine in Step B.

Step B:
6-chloro-4-cyclooctyl-4H-1,2,4-benzothiadiazine 1,1-dioxide

The expected product is obtained according to the process described in Step C of Example 1 (heating time: 48 hours, at 130° C.).
Melting point: 209-211° C.

Step C: 6-chloro-4-cyclooctyl-3,4-dihydro-2H-1,2,4-benzothiadiazine 1,1-dioxide

The expected product is obtained according to the process described in Step D of Example 1.
Melting point: 141-143° C.

EXAMPLE 59

6,7-dichloro-4-(1-methyl)cyclopropyl-3,4-dihydro-2H-1,2,4-benzothiadiazine 1,1-dioxide Step A: 4,5-dichloro-2-(1-methyl)cyclopropylaminobenzenesulphonamide Starting from 4,5-dichloro-2-fluoroaniline, the expected product is obtained according to the process described in Steps A and B of Example 1, with addition of (1-methyl)cyclopropylamine in Step B.
Melting point: 130-132° C.

Step B: 6,7-dichloro-4-(1-methyl)cyclopropyl-4H-1,2,4-benzothiadiazine 1,1-dioxide The expected product is obtained according to the process described in Step C of Example 1 (heating time: 24 hours).
Melting point: 230-232° C.

Step C: 6,7-dichloro-4-(1-methyl)cyclopropyl-2H-1,2,4-benzothiadiazine 1,1-dioxide The expected product is obtained according to the process described in Step D of Example 1.
Melting point: 162-163° C.

EXAMPLE 60

7-chloro-4-cyclopropylmethyl-3,4-dihydro-2H-1,2,4-benzothiadiazine 1,1-dioxide

Step A: 7-chloro-4H-1,2,4-benzothiadiazine 1,1-dioxide

A mixture of 2-amino-5-chlorobenzenesulphonamide (obtained according to J. Chem. Soc. Perkin I, 1043-1047, 1979) and ethyl orthoformate (40 mL) is heated at boiling for 30 minutes in an open vessel. The volume of the mixture is reduced by half under reduced pressure. The precipitate obtained is collected by filtration, washed with ether and dried.
Melting point: 243-244° C.

Step B: 7-chloro-4-cyclopropylmethyl-4H-1,2,4-benzothiadiazine 1,1-dioxide

To a solution of 7-chloro-4H-1,2,4-benzothiadiazine 1,1-dioxide (1 g) in acetonitrile (40 mL) there is added potassium carbonate (2.5 g) and cyclopropylmethyl bromide (0.7 mL)

and the mixture is heated at reflux for 24 hours. The reaction mixture is evaporated under reduced pressure and the residue is taken up in water (40 mL). The insoluble material is collected by filtration, washed with water and dried and is recrystallised from methanol.

Melting point: 183-185° C.

Step C: 7-chloro-4-cyclopropylmethyl-3,4-dihydro-2H-1,2,4-benzothiadiazine 1,1-dioxide To a solution of 7-chloro-4-cyclopropylmethyl-4H-1,2,4-benzothiadiazine 1,1-dioxide (0.7 g) in isopropanol (50 mL) there is added sodium borohydride (0.2 g) and the mixture is heated at 50° C. for 5 minutes. The reaction mixture is evaporated under reduced pressure and the residue is taken up in water (30 mL). The pH of the medium is adjusted to 5-6 by addition of 6N hydrochloric acid and the suspension is extracted three times with chloroform (30 mL). The organic phases are collected, dried over anhydrous $MgSO_4$ and filtered. The filtrate is evaporated under reduced pressure and the residue is taken up in methanol (5 mL). Water (50 mL) is added to the methanolic solution and the precipitate which appears is collected by filtration, washed with water and dried.

Melting point: 106-109° C.

EXAMPLE 61

4-cyclopropylmethyl-7-fluoro-3,4-dihydro-2H-1,2,4-benzothiadiazine 1,1-dioxide

Step A: 7-fluoro-4H-1,2,4-benzothiadiazine 1,1-dioxide

The expected product is obtained according to the process described in Step A of Example 60, starting from 2-amino-5-fluorobenzenesulphonamide.

Melting point: 269-270° C.

Step B: 4-cyclopropylmethyl-7-fluoro-4H-1,2,4-benzothiadiazine 1,1-dioxide

The expected product is obtained according to the process described in Step B of Example 60.

Melting point: 155-157° C.

Step C: 4-cyclopropylmethyl-7-fluoro-3,4-dihydro-2H-1,2,4-benzothiadiazine 1,1-dioxide The expected product is obtained according to the process described in Step C of Example 60.

Melting point: 102-105° C.

EXAMPLE 62

4-cyclopropyl-7,8-difluoro-3,4-dihydro-2H-1,2,4-benzothiadiazine 1,1-dioxide

Step A: 2,3,6-trifluorobenzenesulphonamide

The expected product is obtained according to the process described in Step A of Example 1, starting from 2,3,6-trifluoroaniline.

Melting point: 148-151° C.

Step B: 2-cyclopropylamino-5,6-difluorobenzenesulphonamide

The expected product is obtained according to the process described in Step B of Example 1.

Step C: 4-cyclopropyl-7,8-difluoro-4H-1,2,4-benzothiadiazine 1,1-dioxide

The expected product is obtained according to the process described in Step C of Example 1 (heating time: 2 hours, at 130° C.).

Melting point: 205-206° C.

Step D: 4-cyclopropyl-7,8-difluoro-3,4-dihydro-2H-1,2,4-benzothiadiazine 1,1-dioxide The expected product is obtained according to the process described in Step D of Example 1.

Melting point: 199-201° C.

EXAMPLE 63

6-cyano-4-cyclopropyl-7-fluoro-3,4-dihydro-2H-1,2,4-benzothiadiazine 1,1-dioxide Step A: 2,5-difluoro-4-sulphamoylbenzonitrile The expected product is obtained according to the process described in Step A of Example 1, starting from 4-cyano-2,5-difluoroaniline.

Step B: 2-cyclopropylamino-2-fluoro-4-sulphamoylbenzonitrile

The expected product is obtained according to the process described in Step B of Example 1.

Step C: 6-cyano-4-cyclopropyl-7-fluoro-4H-1,2,4-benzothiadiazine 1,1-dioxide

The expected product is obtained according to the process described in Step C of Example 1 (heating time: 24 hours, at 130° C.).

Melting point: 205-207° C.

Step D: 6-cyano-4-cyclopropyl-7-fluoro-3,4-dihydro-2H-1,2,4-benzothiadiazine 1,1-dioxide The expected product is obtained according to the process described in Step D of Example 1.

Melting point: 208-210° C.

EXAMPLE 64

6-bromo-4-cyclopropyl-8-fluoro-3,4-dihydro-2H-1,2,4-benzothiadiazine 1,1-dioxide Step A: 4-bromo-2,6-difluorobenzenesulphonamide The expected product is obtained according to the process described in Step A of Example 1, starting from 4-bromo-2,6-difluoroaniline.

Melting point: 142-146° C.

Step B: 4-bromo-2-cyclopropylamino-6-fluorobenzenesulphonamide

The expected product is obtained according to the process described in Step B of Example 1.

Step C: 6-bromo-4-cyclopropyl-8-fluoro-4H-1,2,4-benzothiadiazine 1,1-dioxide

The expected product is obtained according to the process described in Step C of Example 1 (heating time: 72 hours, at 130° C.).
Melting point: 285-287° C.

Step D: 6-bromo-4-cyclopropyl-8-fluoro-3,4-dihydro-2H-1,2,4-benzothiadiazine 1,1-dioxide The expected product is obtained according to the process described in Step D of Example 1.
Melting point: 195-198° C.

EXAMPLE 65

6-bromo-4-cyclopropyl-5-fluoro-3,4-dihydro-2H-1,2,4-benzothiadiazine 1,1-dioxide Step A: 4-bromo-2,3-difluorobenzenesulphonamide The expected product is obtained according to the process described in Step A of Example 1, starting from 4-bromo-2,3-difluoroaniline.
Melting point: 155-157° C.

Step B: 4-bromo-2-cyclopropylamino-3-fluorobenzenesulphonamide

The expected product is obtained according to the process described in Step B of Example 1.

Step C: 6-bromo-4-cyclopropyl-5-fluoro-4H-1,2,4-benzothiadiazine 1,1-dioxide

The expected product is obtained according to the process described in Step C of Example 1 (heating time: 3 hours, at 130° C.).
Melting point: 244-247° C.

Step D: 6-bromo-4-cyclopropyl-5-fluoro-3,4-dihydro-2H-1,2,4-benzothiadiazine 1,1-dioxide The expected product is obtained according to the process described in Step D of Example 1.
Melting point: 197-199° C.

EXAMPLE 66

7-bromo-4-cyclopropyl-6-fluoro-3,4-dihydro-2H-1,2,4-benzothiadiazine 1,1-dioxide Step A: 5-bromo-2,4-difluorobenzenesulphonamide The expected product is obtained according to the process described in Step A of Example 1, starting from 5-bromo-2,4-difluoroaniline.
Melting point: 109-111° C.

Step B: 5-bromo-2-cyclopropylamino-4-fluorobenzenesulphonamide

The expected product is obtained according to the process described in Step B of Example 1.

Step C: 7-bromo-4-cyclopropyl-6-fluoro-4H-1,2,4-benzothiadiazine 1,1-dioxide

The expected product is obtained according to the process described in Step C of Example 1 (heating time: 4 hours, at 130° C.).
Melting point: 228-231° C.

Step D: 7-bromo-4-cyclopropyl-6-fluoro-3,4-dihydro-2H-1,2,4-benzothiadiazine 1,1-dioxide The expected product is obtained according to the process described in Step D of Example 1.
Melting point: 175-177° C.

EXAMPLE 67

4-cyclopropyl-5,7,8-trifluoro-3,4-dihydro-2H-1,2,4-benzothiadiazine 1,1-dioxide

Step A: 2-cyclopropylamino-3,5,6-trifluorobenzenesulphonamide

The expected product is obtained according to the process described in Step B of Example 1, starting from commercial 2,3,5,6-tetrafluorobenzenesulphonamide.

Step B: 4-cyclopropyl-5,7,8-trifluoro-4H-1,2,4-benzothiadiazine 1,1-dioxide

The expected product is obtained according to the process described in Step C of Example 1 (heating time: 4 hours, at 130° C.).
Melting point: 166-168° C.

Step C: 4-cyclopropyl-5,7,8-trifluoro-3,4-dihydro-2H-1,2,4-benzothiadiazine 1,1-dioxide The expected product is obtained according to the process described in Step D of Example 1.
Melting point: 149-151° C.

EXAMPLE 68

7-chloro-4-cyclopropyl-6-fluoro-3,4-dihydro-2H-1,2,4-benzothiadiazine 1,1-dioxide Step A: 5-chloro-2-cyclopropylamino-4-fluorobenzenesulphonamide The expected product is obtained according to the process described in Step B of Example 1, starting from commercial 5-chloro-2,4-difluorobenzenesulphonamide.

Step B: 7-chloro-4-cyclopropyl-6-fluoro-4H-1,2,4-benzothiadiazine 1,1-dioxide

The expected product is obtained according to the process described in Step C of Example 1 (heating time: 5 hours, at 130° C.).
Melting point: 21 7-219° C.

Step C: 7-chloro-4-cyclopropyl-6-fluoro-3,4-dihydro-2H-1,2,4-benzothiadiazine 1,1-dioxide The expected product is obtained according to the process described in Step D of Example 1.
Melting point: 155-158° C.

EXAMPLE 69

7-aminocarbonyl-4-cyclopropyl-3,4-dihydro-2H-1,2,4-benzothiadiazine 1,1-dioxide

Step A: 4-fluoro-3-sulphamoylbenzamide

A solution of 4-fluoro-3-sulphamoylbenzoic acid (5.4 mmol) in thionyl chloride (10 mL) is refluxed for 4 hours. The reagent is then removed by distillation under reduced pressure and the residue is re-dissolved in dry toluene (10 mL). The solvent is removed by distillation under reduced pressure. This operation is repeated twice, and then the residue is dissolved in dry dioxane (10 mL), and ammonia (6 mmol) and pyridine (6 mmol) are added. After one hour, the solvent is removed under reduced pressure and the residue is taken up in methanol (5 mL), and then water (30 mL) is added. The precipitate obtained is collected by filtration, washed with water and dried.

Melting point: 212-214° C.

Step B: 4-cyclopropylamino-3-sulphamoylbenzamide

The expected product is obtained according to the process described in Step B of Example 1.

Step C: 7-aminocarbonyl-4-cyclopropyl-4H-1,2,4-benzothiadiazine 1,1-dioxide

The expected product is obtained according to the process described in Step C of Example 1 (heating time: 3 hours, at 130° C.).

Melting point: 278-281° C.

Step D: 7-aminocarbonyl-4-cyclopropyl-3,4-dihydro-2H-1,2,4-benzothiadiazine 1,1-dioxide The expected product is obtained according to the process described in Step D of Example 1.

Melting point: 269-271° C.

EXAMPLE 70

7-aminocarbonyl-4-cyclopropyl-3,4-dihydro-N-methyl-2H-1,2,4-benzothiadiazine 1,1-dioxide Step A: 4-fluoro-N-methyl-3-sulphamoylbenzamide The expected product is obtained according to the process described in Step A of Example 69, using methylamine instead of ammonia.

Melting point: 242-244° C.

Step B: 4-cyclopropylamino-N-methyl-3-sulphamoylbenzamide

The expected product is obtained according to the process described in Step B of Example 1.

Step C: 7-aminocarbonyl-4-cyclopropyl-N-methyl-4H-1,2,4-benzothiadiazine 1,1-dioxide The expected product is obtained according to the process described in Step C of Example 1 (heating time: 3 hours, at 130° C.).

Melting point: 300-305° C.

Step D: 7-aminocarbonyl-4-cyclopropyl-3,4-dihydro-N-methyl-2H-1,2,4-benzothiadiazine 1,1-dioxide The expected product is obtained according to the process described in Step D of Example 1.

Melting point: 271-273° C.

EXAMPLE 71

7-aminocarbonyl-4-cyclopropyl-3,4-dihydro-N,N-dimethyl-2H-1,2,4-benzothiadiazine 1,1-dioxide Step A: 4-fluoro-N,N-dimethyl-3-sulphamoylbenzamide The expected product is obtained according to the process described in Step A of Example 69, using dimethylamine instead of ammonia.

Step B: 4-cyclopropylamino-N,N-dimethyl-3-sulphamoylbenzamide

The expected product is obtained according to the process described in Step B of Example 1.

Step C: 7-aminocarbonyl-4-cyclopropyl-N,N-dimethyl-4H-1,2,4-benzothiadiazine 1,1-dioxide The expected product is obtained according to the process described in Step C of Example 1 (heating time: 3 hours, at 130° C.).

Melting point: 173-175° C.

Step D: 7-aminocarbonyl-4-cyclopropyl-3,4-dihydro-N,N-dimethyl-2H-1,2,4-benzothiadiazine 1,1-dioxide The expected product is obtained according to the process described in Step D of Example 1.

Melting point: 216-219° C.

EXAMPLE 72

8-bromo-6-cyano-4-cyclopropyl-3,4-dihydro-2H-1,2,4-benzothiadiazine 1,1-dioxide

Step A: 3-bromo-5-fluoro-4-sulphamoylbenzonitrile

The expected product is obtained according to the process described in Step A of Example 1, starting from 2-bromo-4-cyano-5-fluoroaniline.

Step B: 3-bromo-5-cyclopropylamino-4-sulphamoylbenzonitrile

The expected product is obtained according to the process described in Step B of Example 1.

Step C: 8-bromo-6-cyano-4-cyclopropyl-4H-1,2,4-benzothiadiazine 1,1-dioxide

The expected product is obtained according to the process described in Step C of Example 1 (heating time: 3 hours, at 130° C.).

Step D: 8-bromo-6-cyano-4-cyclopropyl-3,4-dihydro-2H-1,2,4-benzothiadiazine 1,1-dioxide The expected product is obtained according to the process described in Step D of Example 1.
Melting point: 250-253° C.

EXAMPLE 73

7-amino-4-cyclopropyl-3,4-dihydro-2H-1,2,4-benzothiadiazine 1,1-dioxide

The expected product is obtained according to the process described in Step D of Example 1, starting from 7-amino-4-cyclopropyl-4H-1,2,4-benzothiadiazine 1,1-dioxide prepared in Step A of Example 42.
Melting point: 187-189° C.

EXAMPLE 74

4-cyclopropyl-3,4-dihydro-6-nitro-2H-1,2,4-benzothiadiazine 1,1-dioxide

Step A: 2-fluoro-4-nitrobenzenesulphonamide

The expected product is obtained according to the process described in Step A of Example 41, starting from 2-fluoro-4-nitroaniline.
Melting point: 145-147° C.

Step B: 2-cyclopropylamino-4-nitrobenzenesulphonamide

The expected product is obtained according to the process described in Step B of Example 41.

Step C: 4-cyclopropyl-6-nitro-4H-1,2,4-benzothiadiazine 1,1-dioxide

The expected product is obtained according to the process described in Step C of Example 41.
Melting point: 254-257° C.

Step D: 4-cyclopropyl-3,4-dihydro-6-nitro-2H-1,2,4-benzothiadiazine 1,1-dioxide

The expected product is obtained according to the process described in Step D of Example 1.
Melting point: 166-169° C.

EXAMPLE 75

6-acetamido-4-cyclopropyl-3,4-dihydro-2H-1,2,4-benzothiadiazine 1,1-dioxide

Step A: 6-amino-4-cyclopropyl-4H-1,2,4-benzothiadiazine 1,1-dioxide

The expected product is obtained according to the process described in Step A of Example 42, starting from the compound of Example 74.
Melting point: 177-180° C.

Step B: 6-acetamido-4-cyclopropyl-3,4-dihydro-2H-1,2,4-benzothiadiazine 1,1-dioxide The expected product is obtained according to the process described in Step B of Example 42.
Melting point: 265-267° C.

EXAMPLE 76

6-amino-4-cyclopropyl-3,4-dihydro-2H-1,2,4-benzothiadiazine 1,1-dioxide

The expected product is obtained according to the process described in Step D of Example 1, starting from 6-amino-4-cyclopropyl-4H-1,2,4-benzothiadiazine 1,1-dioxide prepared in Step A of Example 75.
Melting point: 185-188° C.

EXAMPLE 77

4-cyclopropyl-3,4-dihydro-7-methoxycarbonyl-2H-1,2,4-benzothiadiazine 1,1-dioxide Step A: 4-fluoro-3-sulphamoylbenzoic acid A suspension of 2-fluoro-5-methylbenzenesulphonamide (5.3 mmol), obtained according to the process described in Step A of Example 1 starting from 2-fluoro-5-methylaniline, in water (50 mL) is heated at 70° C. and then NaOH 10% w/v is added dropwise until the compound has completely dissolved. Potassium permanganate (3 g) is added in small portions. After stirring for 4 hours, the suspension is discharged by filtration in the hot state and the filtrate is brought to pH 1 by adding 12N HCl. The precipitate obtained is collected by filtration, washed with water and dried to yield the title product in the form of a white solid.
Melting point: 237-239° C.

Step B: methyl 4-cyclopropylamino-3-sulphamoylbenzoate

4-Cyclopropylamino-3-sulphamoylbenzoic acid (3.9 mmol), prepared according to the process described in Step B of Example 1 starting from the compound obtained in the Step above, is then dissolved in sulphuric acid (0.5 mL) and methanol (10 mL), and the mixture is heated at reflux for 4 hours. The solvent is then removed by distillation under reduced pressure and the residue is suspended in water (20 mL). The precipitate obtained is collected by filtration, washed with water and dried to yield the title product in the form of a white solid.
Melting point: 158-161° C.

Step C: 4-cyclopropyl-7-methoxycarbonyl-4H-1,2,4-benzothiadiazine 1,1-dioxide

The expected product is obtained according to the process described in Step C of Example 1 (heating time: 4 hours at 130° C.).
Melting point: 192-195° C.

Step D: 4-cyclopropyl-3,4-dihydro-7-methoxycarbonyl-2H-1,2,4-benzothiadiazine 1,1-dioxide The expected product is obtained according to the process described in Step D of Example 1.
Melting point: 178-180° C.

EXAMPLE 78

7-carboxy-4-cyclopropyl-3,4-dihydro-2H-1,2,4-benzothiadiazine 1,1-dioxide

A solution of the compound of Example 77 (3.5 mmol) in a mixture of methanol/water 1/1 (100 mL) containing NaOH (0.5 g) is heated at 40° C. for 3 hours. The methanol is then removed by distillation under reduced pressure and the resulting aqueous solution is adjusted to pH 2 by adding 6N HCl. The precipitate obtained is collected by filtration, washed with water and dried to yield the title product in the form of a white solid.
Melting point: 263-265° C.

EXAMPLE 79

4-cyclopropyl-3,4-dihydro-7-phenoxycarbonyl-2H-1,2,4-benzothiadiazine 1,1-dioxide N,N'-carbonyldiimidazole (0.6 g) is added to a solution of the compound of Example 78 (3.5 mmol) in DMF (7 mL). After stirring for 1 hour at ambient temperature, phenol (0.5 g) and DBU (0.5 mL) are added. After stirring for 2 hours at ambient temperature, water (40 mL) is added and the mixture is extracted three times with ethyl acetate (30 mL). The organic phases are combined, dried over anhydrous $MgSO_4$ and filtered. The filtrate is evaporated to dryness and the residue is re-dissolved in methanol (5 mL). Water (50 mL) is added to the solution and the precipitate obtained is collected by filtration, washed with water and dried to yield the title product in the form of a white solid.
Melting point: 160-162° C.

EXAMPLE 80

4-cyclopropyl-3,4-dihydro-6-methoxycarbonyl-2H-1,2,4-benzothiadiazine 1,1-dioxide Step A: methyl 3-fluoro-4-sulphamoylbenzoate A solution of 3-fluoro-4-sulphamoylbenzoic acid (4.5 mmol), obtained in 2 steps according to the process described in Step A of Example 77, starting from 2-fluoro-4-methylaniline, and sulphuric acid (0.5 mL) in methanol (10 mL) is heated at reflux for 1 hour. The solvent is then removed by distillation under reduced pressure and the residue is suspended in water (20 mL). The precipitate obtained is collected by filtration, washed with water and dried to yield the title product in the form of a white solid.
Melting point: 153-156° C.

Step B: methyl 3-cyclopropylamino-4-sulphamoylbenzoate

The expected product is obtained according to the process described in Step B of Example 1.

Step C: 4-cyclopropyl-6-methoxycarbonyl-4H-1,2,4-benzothiadiazine 1,1-dioxide

The expected product is obtained according to the process described in Step C of Example 1 (heating time: 4 hours, at 130° C.).
Melting point: 191-194° C.

Step D: 4-cyclopropyl-3,4-dihydro-6-methoxycarbonyl-2H-1,2,4-benzothiadiazine 1,1-dioxide The expected product is obtained according to the process described in Step D of Example 1.
Melting point: 162-164° C.

EXAMPLE 81

6-carboxy-4-cyclopropyl-3,4-dihydro-2H-1,2,4-benzothiadiazine 1,1-dioxide

The expected product is obtained according to the process described in Example 78, using the compound of Example 80 as starting material instead of the compound of Example 77.
Melting point: 243-245° C.

EXAMPLE 82

4-cyclopropyl-3,4-dihydro-7-phenylaminocarbonyl-2H-1,2,4-benzothiadiazine 1,1-dioxide Step A: 4-fluoro-N-phenyl-3-sulphamoylbenzamide The expected product is obtained in 4 steps, starting from 4-fluoro-3-nitrotoluene. The 4-fluoro-3-nitrotoluene (6.5 mmol) is added in small portions to a solution of potassium dichromate (4 g) in glacial acetic acid (10 mL). After stirring for 15 minutes, sulphuric acid (4 mL) is added and the solution is heated at reflux for 2 hours. The mixture is then cooled, water (100 mL) is added and extraction with ethyl acetate (3×100 mL) is carried out. The organic phases are collected, dried over anhydrous $MgSO_4$ and evaporated. The residue is recrystallised from an ethyl acetate/hexane (1/1) mixture and used in the next step.

A solution of the 4-fluoro-3-nitrobenzoic acid (5.4 mmol) in thionyl chloride (10 mL) is heated at reflux for 4 hours. After evaporating off the solvent under reduced pressure, the residue is re-dissolved in dry toluene (10 mL) and the solution is evaporated to dryness. This operation is repeated twice. The residue is dissolved in dry dioxane (10 mL), and aniline (6 mmol) and pyridine (6 mmol) are added to the solution. After stirring for 1 hour at ambient temperature, the solvent is removed under reduced pressure and the residue is dissolved in methanol (5 mL). Water (30 mL) is added to the resulting solution and the precipitate obtained is collected by filtration, washed with water and dried for use in the next step.

A suspension of the 4-fluoro-3-nitro-N-phenylbenzamide (4 mmol) in an ethanol/water (2/1) mixture is heated to reflux and then ammonium chloride (0.5 g) and iron powder (2 g) are added. After 15 minutes, the suspension is filtered in the warm state and the insoluble material is rinsed with warm ethanol (50 mL). The filtrate is treated with absorbent carbon and filtered. The ethanol in the filtrate is removed by distillation under reduced pressure. The precipitate obtained is collected by filtration, washed with water and dried.

The product thereby obtained is reacted according to the process described in Step A of Example 1 to yield the title product.
Melting point: 219-221° C.

Step B:
4-cyclopropylamino-N-phenyl-3-sulphamoylbenzamide

The expected product is obtained according to the process described in Step B of Example 1.

Step C: 4-cyclopropyl-7-phenylaminocarbonyl-4H-1, 2,4-benzothiadiazine 1,1-dioxide The expected product is obtained according to the process described in Step C of Example 1 (heating time: 4 hours, at 130° C.).
Melting point: 293-296° C.

Step D: 4-cyclopropyl-3,4-dihydro-7-phenylaminocarbonyl-2H-1,2,4-benzothiadiazine 1,1-dioxide The expected product is obtained according to the process described in Step D of Example 1.
Melting point: 268-270° C.

EXAMPLE 83

4-cyclopropyl-3,4-dihydro-6-phenylaminocarbonyl-2H-1,2,4-benzothiadiazine 1,1-dioxide Step A: 3-fluoro-N-phenyl-4-sulphamoylbenzamide The expected product is obtained according to the process described in Step A of Example 82, starting from 3-fluoro-4-nitrotoluene.
Melting point: 250-252° C.

Step B:
3-cyclopropylamino-N-phenyl-4-sulphamoylbenzamide

The expected product is obtained according to the process described in Step B of Example 1.

Step C: 4-cyclopropyl-6-phenylaminocarbonyl-4H-1, 2,4-benzothiadiazine 1,1-dioxide The expected product is obtained according to the process described in Step C of Example 1 (heating time: 4 hours, at 130° C.).
Melting point: 278-281° C.

Step D: 4-cyclopropyl-3,4-dihydro-6-phenylaminocarbonyl-2H-1,2,4-benzothiadiazine 1,1-dioxide The expected product is obtained according to the process described in Step D of Example 1.
Melting point: 232-234° C.

EXAMPLE 84

4-cyclopropyl-3,4-dihydro-7-methoxy-2H-1,2,4-benzothiadiazine 1,1-dioxide

Step A:
2-cyclopropylamino-5-methoxybenzenesulphonamide

To a solution of 2-amino-5-methoxybenzenesulphonamide (4.9 mmol) in methanol (20 mL) there are added (1-ethoxycyclopropyloxy)trimethylsilane (4 mL) and glacial acetic acid (4 mL) and then heating at reflux is carried out for 18 hours. The mixture is then evaporated to dryness under reduced pressure. The oil obtained is taken up in water (30 mL) and extracted with chloroform (3×30 mL). The organic phases are collected and dried over anhydrous $MgSO_4$. After filtration, the filtrate is evaporated to dryness and the residual oil is dissolved in THF (50 mL). Sodium borohydride (2 g) and boron trifluoride etherate (2 mL) are added and then the mixture is heated at reflux for 18 hours. The solvent is then removed by evaporation under reduced pressure and the residue is taken up in water (30 mL), adjusted to slightly acid pH by adding 6N HCl and then extracted with chloroform (3×30 mL). The organic phases are collected and dried over anhydrous $MgSO_4$. After filtration, the filtrate is evaporated to dryness and the expected compound is obtained in the form of an oil used directly in the next Step.

Step B:
4-cyclopropyl-7-methoxy-4H-1,2,4-benzothiadiazine 1,1-dioxide

The expected product is obtained according to the process described in Step C of Example 1.
Melting point: 216-219° C.

Step C: 4-cyclopropyl-3,4-dihydro-7-methoxy-2H-1, 2,4-benzothiadiazine 1,1-dioxide The expected product is obtained according to the process described in Step D of Example 1.
Melting point: 154-156° C.

EXAMPLE 85

4-cyclopropyl-3,4-dihydro-7-hydroxy-2H-1,2,4-benzothiadiazine 1,1-dioxide

A solution of the compound of Example 84 (50 mg) in chloroform (3 mL) is cooled on an ice bath and then boron tribromide (0.15 mL) is added. After stirring for 20 hours, water (5 mL) is added to the mixture, which is then concentrated under reduced pressure and subsequently extracted with ethyl acetate (3×20 mL). The organic phases are collected and dried over anhydrous $MgSO_4$. After filtration, the filtrate is evaporated to dryness and the residue is dissolved in ethyl acetate (1 mL); hexane (5 mL) is then added. The precipitate obtained is collected by filtration, washed with hexane and dried to yield the expected product in the form of a white solid.
Melting point: 187-189° C.

EXAMPLE 86

6-chloro-4-cyclopropyl-3,4-dihydro-7-methoxy-2H-1,2,4-benzothiadiazine 1,1-dioxide The expected product is obtained according to the process described in Steps A, B and C of Example 84, using 2-amino-4-chloro-5-methoxybenzenesulphonamide as starting material instead of 2-amino-5-methoxybenzenesulphonamide.
Melting point: 188-190° C.

EXAMPLE 87

6-chloro-4-cyclopropyl-3,4-dihydro-7-hydroxy-2H-1,2,4-benzothiadiazine 1,1-dioxide The expected product is obtained according to the process described in Example 85, using the compound of Example 86 as starting material instead of the compound of Example 84.
Melting point: 213-214° C.

EXAMPLE 88

6,7-dichloro-4-cyclopropylmethyl-3,4-dihydro-2H-1,2,4-benzothiadiazine 1,1-dioxide Step A: 6,7-dichloro-4H-1,2,4-benzothiadiazine 1,1-dioxide The expected product is obtained according to the process described in Step A of Example 60, starting from 2-amino-4,5-dichlorobenzenesulphonamide.
Melting point: 237-240° C.

Step B: 6,7-dichloro-4-cyclopropylmethyl-4H-1,2,4-benzothiadiazine 1,1-dioxide

The expected product is obtained according to the process described in Step B of Example 60.
Melting point: 192-195° C.

Step C: 6,7-dichloro-4-cyclopropylmethyl-3,4-dihydro-2H-1,2,4-benzothiadiazine 1,1-dioxide The expected product is obtained according to the process described in Step C of Example 60.
Melting point: 171-173° C.

EXAMPLE 89

5-chloro-4-cyclopropyl-8-fluoro-3,4-dihydro-2H-1,2,4-benzothiadiazine 1,1-dioxide The expected product is obtained according to the process described in steps A, B, C and D of Example 1, starting from 3-chloro-2,6-difluoroaniline.
Melting point: 171-174° C.

EXAMPLE 90

4-cyclopropyl-6,7-difluoro-3,4-dihydro-2H-1,2,4-benzothiadiazine 1,1-dioxide

The expected product is obtained according to the process described in Steps A, B and C of Example 84, using 2-amino-4,5-difluorobenzenesulphonamide as starting material instead of 2-amino-5-methoxybenzenesulphonamide.
Melting point: 146-148° C.

Pharmacological Study

EXAMPLE A

Study of the Effect of Compounds on the Ionic Current Brought About by AMPA in Primary Cultures of Rat Neurons The test comprises the in vitro measurement, by means of fluorescence, of the membrane depolarisation brought about in cultured rat embryonic neurons by the joint action of AMPA and the compound under test, compared to the action of AMPA alone. The brain cells are placed in culture and kept in a cell culture incubator for 18 days. After incubation, the culture medium is withdrawn and replaced with fluorescent probe loading medium for measurement of the membrane potential (20 µl; membrane potential kit from Molecular Devices) and left at ambient temperature for 1 hour. The base fluorescence of the wells is read (FDSS apparatus from Hamamatsu) and the cells are then injected with AMPA (20 µl; concentration range: from 3 to 100 µM) and the action of the AMPA is measured kinetically. The test compound is then introduced into the wells (20 µl; in a concentration range crossed with that of AMPA) and the action of the compound is measured kinetically. At the end of each of the two periods of kinetic measurement, the result for each well is the average reading over the final 15 seconds of the period. The curves are plotted of the effect of AMPA at the various concentrations of compound. For each concentration of compound, the result is the area under the AMPA curve at that concentration, and the $EC_{2X}$ (the concentration of compound which doubles the membrane potential brought about by AMPA) is calculated.

The compounds of the invention greatly potentiate the excitatory effects of AMPA, as the Table below shows for some Examples of compounds of the present invention:

|  | $EC_{2X}(\mu M)$ |
| --- | --- |
| Example 1 | 1.0 |
| Example 2 | 5.0 |
| Example 21 | 2.0 |
| Example 34 | 1.8 |
| Example 37 | 4.4 |
| Example 39 | 4.8 |
| Example 62 | 0.8 |

EXAMPLE B

Object Recognition in the CD1 Mouse

The object recognition test (Behav. Brain Res., 1988, 31, 47-59) is based on the spontaneous exploratory activity of the animal and has the characteristics of episodic memory in humans. This memory test is sensitive to ageing (Eur. J. Pharmacol., 1997, 325, 173-180) and to cholinergic dysfunctions (Pharm. Biochem. Behav. 1996, 53(2), 277-283) and is based on the differences in the exploration of 2 objects of fairly similar shape—one familiar, the other new. The test procedure, which has been adapted for the CD1 mouse, comprises 3 phases which take place in the same test enclosure. During the first phase, which lasts 40 minutes, the mice are habituated to the environment. During the second phase, which takes place the next day, an object is placed in the enclosure and the mouse is free to explore it. Once the duration of that exploration has reached 20 seconds, the mouse is taken out of the enclosure. In the course of the third phase (5 minutes), 24 hours later, the same object is presented (acquiring the status of a "familiar" object), as well as a new object. The duration of exploration, expressed in seconds, is timed for each of the two objects. The control animals, which have previously been given the carrier by the oral route 60 minutes before each of the 3 phases, explore the "familiar" object and the "new" object for an equivalent period, which indicates that the object previously presented has been forgotten. Animals having received a compound that facilitates mnemocognition explore the new object preferentially, which indicates that the memory of the object previously presented has been retained.

The results obtained with the compounds of the present invention show that, at doses of 1 and 3 mg/kg PO, there is significantly more exploration of the new object than of the familiar object, doubling or even tripling the duration of exploration, which indicates that the compounds of the invention greatly enhance memorisation.

For example, the difference in the exploration of the 2 objects in the course of the third phase is contained between 5 and 10 seconds after the administration of the compound of Example 1 whereas the difference is below 3 seconds after administration of the carrier.

EXAMPLE C

Pharmaceutical Composition

| | |
|---|---|
| Formula for the preparation of 1000 tablets each containing 10 mg of 6,7-dichloro-4-cyclopropyl-3,4-dihydro-2H-1,2,4-benzothiadiazine 1,1-dioxide (Example 1) | 10 g |
| Hydroxypropylcellulose | 2 g |
| Wheat starch | 10 g |
| Lactose | 100 g |
| Magnesium stearate | 3 g |
| Talc | 3 g |

The invention claimed is:
1. A compound selected from those of formula (I):

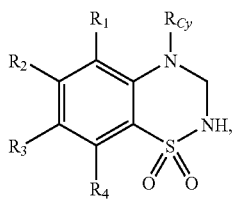

(I)

wherein:
$R_{Cy}$ represents:
  a $(C_3-C_8)$cycloalkyl group which is unsubstituted or substituted by one or more identical or different groups selected from linear or branched $(C_1-C_6)$alkyl which is unsubstituted or substituted by one or more halogen atoms; linear or branched $(C_1-C_6)$alkoxy; hydroxy; and amino which is unsubstituted or substituted by one or two linear or branched $(C_1-C_6)$alkyl groups;
  or a $(C_3-C_8)$cycloalkyl-$(C_1-C_6)$alkyl group in which the alkyl moiety is linear or branched and which is unsubstituted or substituted on the cyclic moiety by one or more identical or different groups selected from linear or branched $(C_1-C_6)$alkyl which is unsubstituted or substituted by one or more halogen atoms; linear or branched $(C_1-C_6)$alkoxy; hydroxy; and amino which is unsubstituted or substituted by one or two linear or branched $(C_1-C_6)$alkyl groups;
$R_1$, $R_2$, $R_3$ and $R_4$, which may be the same or different, each represent a hydrogen atom; a halogen atom; a nitro group; a cyano group; a hydroxy group; a linear or branched $(C_1-C_6)$alkyl group which is unsubstituted or substituted by one or more halogen atoms; a linear or branched $(C_1-C_6)$cyanoalkyl group; a linear or branched $(C_1-C_6)$hydroxyalkyl group; a linear or branched $(C_1-C_6)$alkoxy group which is unsubstituted or substituted by one or more halogen atoms; a linear or branched $(C_1-C_6)$alkylthio group; a carboxy group; a linear or branched $(C_1-C_6)$alkoxycarbonyl group; an aryloxycarbonyl group; a linear or branched $(C_1-C_6)$acyl group; an amino group which is unsubstituted or substituted by one or two linear or branched $(C_1-C_6)$alkyl groups or by a linear or branched $(C_1-C_6)$acyl group; an aminocarbonyl group which is unsubstituted or substituted by one or two linear or branched $(C_1-C_6)$alkyl groups; an arylaminocarbonyl group; or a linear or branched $(C_1-C_6)$alkylsulphonylamino group;

its enantiomers, diastereoisomers, and addition salts thereof with a pharmaceutically acceptable acid or base, it being understood that:
"aryl" means a phenyl group which is unsubstituted or substituted by one or more identical or different groups selected from linear or branched $(C_1-C_6)$alkyl which is unsubstituted or substituted by one or more halogen atoms; linear or branched $(C_1-C_6)$alkoxy; hydroxy; and amino which is unsubstituted or substituted by one or two linear or branched $(C_1-C_6)$alkyl groups.

2. The compound of claim 1, wherein $R_{Cy}$ represents a $(C_3-C_8)$cycloalkyl group.

3. The compound of claim 1, wherein $R_{Cy}$ represents a cyclopropyl group.

4. The compound of claim 1, wherein $R_{Cy}$ represents a $(C_3-C_8)$cycloalkyl-$(C_1-C_6)$alkyl group in which the alkyl moiety is linear or branched.

5. The compound of claim 1, wherein $R_{Cy}$ represents a cyclopropylmethyl group.

6. The compound of claim 1, wherein $R_1$ represents a hydrogen atom or a halogen atom.

7. The compound of claim 1, wherein $R_2$ represents a hydrogen atom, a halogen atom, a methyl group, a cyano group or a carboxy group.

8. The compound of claim 1, wherein $R_3$ represents a hydrogen atom, a halogen atom or a methyl group.

9. The compound of claim 1, wherein $R_4$ represents a hydrogen atom or a halogen atom.

10. The compound of claim 1, wherein two of the groups $R_1$, $R_2$, $R_3$ and $R_4$ are other than a hydrogen atom.

11. The compound of claim 1, wherein two of the groups $R_1$, $R_2$, $R_3$ and $R_4$ represent a halogen atom and $R_{Cy}$ represents a cyclopropyl group.

12. The compound of claim 1, which is selected from:
  6,7-dichloro-4-cyclopropyl-3,4-dihydro-2H-1,2,4-benzothiadiazine 1,1-dioxide;
  8-chloro-4-cyclopropyl-6-fluoro-3,4-dihydro-2H-1,2,4-benzothiadiazine 1,1-dioxide;
  8-bromo-4-cyclopropyl-6-fluoro-3,4-dihydro-2H-1,2,4-benzothiadiazine 1,1-dioxide;
  6-cyano-4-cyclopropyl-3,4-dihydro-2H-1,2,4-benzothiadiazine 1,1-dioxide;
  8-bromo-6-chloro-4-cyclopropyl-3,4-dihydro-2H-1,2,4-benzothiadiazine 1,1-dioxide;
  4-cyclopropyl-5-fluoro-3,4-dihydro-2H-1,2,4-benzothiadiazine 1,1-dioxide;
  8-bromo-4-cyclopropyl-3,4-dihydro-2H-1,2,4-benzothiadiazine 1,1-dioxide;
  4-cyclopropyl-5,7-difluoro-3,4-dihydro-2H-1,2,4-benzothiadiazine 1,1-dioxide;
  6-fluoro-4-cyclopropyl-3,4-dihydro-2H-1,2,4-benzothiadiazine 1,1-dioxide;

8-chloro-4-cyclopropyl-7-fluoro-3,4-dihydro-2H-1,2,4-benzothiadiazine 1,1-dioxide;
4-cyclopropyl-3,4-dihydro-6-methyl-2H-1,2,4-benzothiadiazine 1,1-dioxide;
4-cyclopropyl-8-fluoro-3,4-dihydro-2H-1,2,4-benzothiadiazine 1,1-dioxide;
8-chloro-4-cyclopropyl-3,4-dihydro-2H-1,2,4-benzothiadiazine 1,1-dioxide;
6-bromo-4-cyclopropyl-7-fluoro-3,4-dihydro-2H-1,2,4-benzothiadiazine 1,1-dioxide;
6-bromo-4-cyclopropyl-3,4-dihydro-2H-1,2,4-benzothiadiazine 1,1-dioxide;
4-cyclopropyl-6,8-difluoro-3,4-dihydro-2H-1,2,4-benzothiadiazine 1,1-dioxide;
4-cyclopropyl-5,6-difluoro-3,4-dihydro-2H-1,2,4-benzothiadiazine 1,1-dioxide;
4-cyclopropyl-3,4-dihydro-7-methyl-2H-1,2,4-benzothiadiazine 1,1-dioxide;
6-chloro-4-cyclopropyl-3,4-dihydro-2H-1,2,4-benzothiadiazine 1,1-dioxide;
4-cyclopropyl-3,4-dihydro-6-iodo-2H-1,2,4-benzothiadiazine 1,1-dioxide;
6,7-dichloro-4-(1-methyl)cyclopropyl-3,4-dihydro-2H-1,2,4-benzothiadiazine 1,1-dioxide;
4-cyclopropylmethyl-7-fluoro-3,4-dihydro-2H-1,2,4-benzothiadiazine 1,1-dioxide;
6-carboxy-4-cyclopropyl-3,4-dihydro-2H-1,2,4-benzothiadiazine 1,1-dioxide;
4-cyclopropyl-7,8-difluoro-3,4-dihydro-2H-1,2,4-benzothiadiazine 1,1-dioxide;
8-bromo-6-cyano-4-cyclopropyl-3,4-dihydro-2H-1,2,4-benzothiadiazine 1,1-dioxide;
7-bromo-4-cyclopropyl-3,4-dihydro-2H-1,2,4-benzothiadiazine 1,1-dioxide,
and addition salts with a pharmaceutically acceptable acid or base.

13. A compound selected from those of formula (IV):

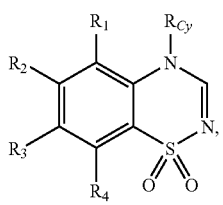

(IV)

wherein:
$R_{Cy}$ represents:
a $(C_3-C_8)$cycloalkyl group which is unsubstituted or substituted by one or more identical or different groups selected from linear or branched $(C_1-C_6)$alkyl which is unsubstituted or substituted by one or more halogen atoms; linear or branched $(C_1-C_6)$alkoxy; hydroxy; and amino which is unsubstituted or substituted by one or two linear or branched $(C_1-C_6)$alkyl groups;
or a $(C_3-C_8)$cycloalkyl-$(C_1-C_6)$alkyl group in which the alkyl moiety is linear or branched and which is unsubstituted or substituted on the cyclic moiety by one or more identical or different groups selected from linear or branched $(C_1-C_6)$alkyl which is unsubstituted or substituted by one or more halogen atoms; linear or branched $(C_1-C_6)$alkoxy; hydroxy; and amino which is unsubstituted or substituted by one or two linear or branched $(C_1-C_6)$alkyl groups;
$R_1$, $R_2$, $R_3$ and $R_4$, which may be the same or different, each represent a hydrogen atom; a halogen atom; a nitro group; a cyano group; a hydroxy group; a linear or branched $(C_1-C_6)$alkyl group which is unsubstituted or substituted by one or more halogen atoms; a linear or branched $(C_1-C_6)$cyanoalkyl group; a linear or branched $(C_1-C_6)$hydroxyalkyl group; a linear or branched $(C_1-C_6)$alkoxy group which is unsubstituted or substituted by one or more halogen atoms; a linear or branched $(C_1-C_6)$alkylthio group; a carboxy group; a linear or branched $(C_1-C_6)$alkoxycarbonyl group; an aryloxycarbonyl group; a linear or branched $(C_1-C_6)$acyl group; an amino group which is unsubstituted or substituted by one or two linear or branched $(C_1-C_6)$alkyl groups or by a linear or branched $(C_1-C_6)$acyl group; an aminocarbonyl group which is unsubstituted or substituted by one or two linear or branched $(C_1-C_6)$alkyl groups; an arylaminocarbonyl group; or a linear or branched $(C_1-C_6)$alkylsulphonylamino group;
its enantiomers, diastereoisomers, and addition salts thereof with a pharmaceutically acceptable acid or base,
it being understood that:
"aryl" means a phenyl group which is unsubstituted or substituted by one or more identical or different groups selected from linear or branched $(C_1-C_6)$alkyl which is unsubstituted or substituted by one or more halogen atoms; linear or branched $(C_1-C_6)$alkoxy; hydroxy; and amino which is unsubstituted or substituted by one or two linear or branched $(C_1-C_6)$alkyl groups.

14. A pharmaceutical composition comprising as active ingredient a compound of claim 1 in combination with one or more inert, non-toxic, pharmaceutically acceptable carriers.

15. A method for treating a condition selected from anxiety, depression, with Parkinson's disease, Pick's disease, Huntington's chorea, Korsakoff's disease, and schizophrenia, such method comprising the step of administering to a living animal body, including a human, a therapeutically effective amount of a compound of claim 1.

* * * * *

UNITED STATES PATENT AND TRADEMARK OFFICE
CERTIFICATE OF CORRECTION

| | | |
|---|---|---|
| PATENT NO. | : 7,741,320 B2 | Page 1 of 1 |
| APPLICATION NO. | : 12/459844 | |
| DATED | : June 22, 2010 | |
| INVENTOR(S) | : Francotte et al. | |

It is certified that error appears in the above-identified patent and that said Letters Patent is hereby corrected as shown below:

Column 54, Line 49:  "depression, with Parkinson's disease," should be
--depression, Parkinson's disease--.

Signed and Sealed this
Tenth Day of May, 2011

David J. Kappos
*Director of the United States Patent and Trademark Office*